US007053245B2

(12) United States Patent
Jolidon et al.

(10) Patent No.: US 7,053,245 B2
(45) Date of Patent: *May 30, 2006

(54) N-ACYLAMINO BENZYL ETHER DERIVATIVES

(75) Inventors: Synese Jolidon, Blauen (CH); Rosa Maria Rodriguez Sarmiento, Basel (CH); Andrew William Thomas, Birsfelden (CH); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 89 days.

This patent is subject to a terminal disclaimer.

(21) Appl. No.: 10/839,514

(22) Filed: May 5, 2004

(65) Prior Publication Data

US 2004/0210079 A1 Oct. 21, 2004

Related U.S. Application Data

(63) Continuation of application No. 10/445,580, filed on May 27, 2003, now Pat. No. 6,762,320.

(30) Foreign Application Priority Data

May 29, 2002 (EP) ............................ 02011639

(51) Int. Cl.
C07C 233/05 (2006.01)

(52) U.S. Cl. ........................ 564/157; 564/143; 564/158; 562/455; 558/392; 514/520; 514/521; 514/535; 514/616

(58) Field of Classification Search ................ 564/143, 564/157, 158; 562/455; 558/392; 514/520, 514/521, 535, 616
See application file for complete search history.

(56) References Cited

U.S. PATENT DOCUMENTS 5,416,112 A * 5/1995 Kuo ............................ 514/521
6,762,320 B1 * 7/2004 Jolidon et al. ............... 564/157

FOREIGN PATENT DOCUMENTS

| DE | 10 03 753   | 3/1957  |
| EP | 0 632 017   | 1/1995  |
| JP | 5262718     | 10/1993 |
| WO | WO 96/40095 | 12/1996 |
| WO | WO 97/33572 | 9/1997  |
| WO | WO 01/34172 | 5/2001  |

OTHER PUBLICATIONS

Bach, A. W. et al., Proc. Natl. Acad. Sci. USA 1988, 85, pp. 4934–4938.
Cesura A. M. & Pletscher A., Prog. Drug Research 1992, 38 pp. 171–297.
Fowler, C. J. et al., J. Neural. Transm. 1980, 49, pp. 1–20.
Dostert P. et al., Biochem. Pharmacol. 1989, 38, pp. 555–561.
Saura et al., Neuroscience, 1996, 70, pp. 755–774.
Bentué–Ferrer D. et al., CNS Drugs, 1996, 6, pp. 217–236.
Gardner D. M. et al., J. Clin. Psychiatry, 1996, 57, pp. 99–104.
Bentley et al., J. Chem. Soc. (C) 1969, pp. 2233–2234.
Krishnamurthy et al., Tetrahedron Lett. 1982, 23, pp. 3315–3318.
Lam et al., Tetrahedron Lett., 2002, 43, pp. 3091–3094.
Lam et al., Synlett, 2000, 5, pp. 674–676.
Chan et al., Tetrahedron Lett. 1998, 39, pp. 2933–2936.
Wolfe et al., J. Amer. Chem. Soc., 1996, 118, pp. 7215–7216.
Schlaeger E.–J. & Christensen K. (Transient Gene Expression in Mammalian Cells Grown in Serum Free Suspension Culture); Cytotechnology, 30: 71–83, 1999.
Zhou M. & Panchuk N.—Voloshina (A One–Step Fluorometric Method for the Continuous Measurement of Monoamine Oxidase Activity), Analytical Biochemistry 253: 169–174, 1997.
Ehrhardt, Jean Daniel, et al., European Journal of Medicinal Chemistry, 13(3), pp. 235–240 (1978), XP009018741.
Trivedi, J.P., et al., Indian Journal of Applied Chemistry, 30(3–4), pp. 91–95 (1967), XP009018747.
Lukas, A., et al., Acta Facultatis Pharmaceuticae Universitatis Comenianae, vol. 28, pp. 91–114 (1975), XP001155612.
Lukas, A., et al., Ceskoslov. Farm., vol. 13, pp. 225–228 (1964), XP009018756.

(Continued)

*Primary Examiner*—Shailendra Kumar
(74) *Attorney, Agent, or Firm*—George W. Johnston; Patricia S. Rocha-Tramaloni; Kimberly J. Prior

(57) ABSTRACT

This invention relates to N-acylamino aryl derivatives of the formula

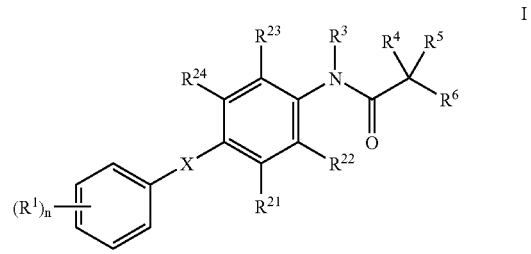

where
$R^1$, $R^{21}$, $R^{22}$, $R^{23}$, $R^{24}$, $R^3$, $R^4$, $R^5$, $R^6$, $R^7$, $R^8$, R, and n are as defined herein and where
X is —CHRO, —OCHR—, —$CH_2S$—, —$SCH_2$—, —$CH_2CH_2$—, —CH=CH— or —C≡C—.
The compounds of the invention are selective monoamine oxidase B inhibitors, and they are therefore useful in the treatment of diseases mediated by monoamine oxidase B, for example, for the treatment of Alzheimer's disease or senile dementia.

10 Claims, No Drawings

OTHER PUBLICATIONS

Lukas, A., et al., et al., Ceskoslovenska Farmacie, vol. 21, No. 6, pp. 273–275 (1972), XP009018758.

Lukas, A., et al., Acta Facultatis Pharmaceuticae Bohemoslovenicae, vol. 12, pp. 189–202 (1966), XP001155535.

Kalgutkar, A.S., et al., Medicinal Research Reviews, vol. 15, No. 4, pp. 325–388 (1995), XP002034298.

Dostert, P., et al., International Congress Series, vol. 564, pp. 197–208 (1982), XP001027632.

Abstract corresponding to JP 5262718.

* cited by examiner

N-ACYLAMINO BENZYL ETHER DERIVATIVES

PRIORITY TO RELATED APPLICATIONS

This application is a Continuation of Ser. No. 10/445,580, filed May 27, 2003, now U.S. Pat. No. 6,762,320.

FIELD OF THE INVENTION

The present invention relates to new N-acylamino aryl derivatives, to processes and intermediates for their preparation, and to pharmaceutical compositions containing them. These compounds are selective monoamine oxidase inhibitors and, therefore, are useful for treating or preventing diseases mediated by monoamine oxidase B.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes (A. W. Bach et al., *Proc. Natl. Acad. Sci. USA* 1988, 85, 4934–4938) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (A. M. Cesura and A. Pletscher, *Prog. Drug Research* 1992, 38, 171–297). Brain MAO-B activity appears to increase with age. This increase has been attributed to the gliosis associated with aging (C. J. Fowler et al., *J. Neural. Transm.* 1980, 49, 1–20). Additionally, MAO-B activity is significantly higher in the brains of patients with Alzheimer's disease (P. Dostert et al., *Biochem. Pharmacol.* 1989, 38, 555–561) and it has been found to be highly expressed in astrocytes around senile plaques (Saura et al., *Neuroscience* 1994, 70, 755–774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentué-Ferrer et al. in *CNS Drugs* 1996, 6, 217–236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., *J. Clin. Psychiatry* 1996, 57, 99–104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

It is an object of the present invention to provide compounds having the following formula:

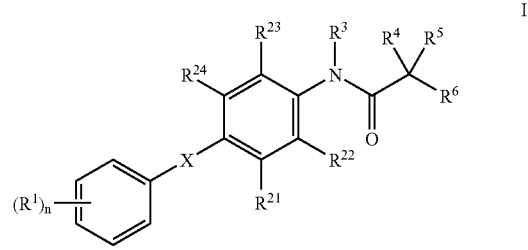

in which X is —CHRO—, —OCHR—, —CH$_2$S—, —SCH$_2$—, —CH$_2$CH$_2$—, —CH=CH or —C≡C—, and the other variables are defined herein. The invention also provides for pharmaceutically acceptable salts of these compounds.

It has been found that the compounds of the invention are highly selective MAO-B inhibitors. Therefore, it is another object of the invention to provide compositions containing one or more compounds of formula I and a pharmaceutically acceptable carrier. It a further object of the invention to provide methods for the treatment or prevention of diseases mediated by monoamine oxidase B inhibitors. It is also an object of the present invention to provide a process for the manufacture of compounds of the invention, for example, compounds of formula I.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "$(C_1$–$C_6)$-alkyl" ("lower alkyl") used in the present application denotes straight-chain or branched saturated hydrocarbon residues with 1 to 6 carbon atoms, preferably with 1 to 3 carbon atoms, such as methyl, ethyl, n-propyl, i-propyl, n-butyl, sec-butyl, t-butyl, and the like. Accordingly, the term "$(C_1$–$C_3)$-alkyl" means a straight-chain or branched saturated hydrocarbon residue with 1 to 3 carbon atoms.

The term "halogen" denotes fluorine, chlorine, bromine and iodine.

"Halogen-$(C_1$–$C_6)$-alkyl" or "halogen-$(C_1$–$C_6)$-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like."

Halogenalkoxy" includes trifluoromethyloxy.

"$(C_1-C_6)$-Alkoxy" means the residue —O—R, wherein R is a lower alkyl residue as defined herein. Examples of alkoxy radicals include, but are not limited to, methoxy, ethoxy, isopropoxy, and the like.

The term "$(C_3-C_7)$-cycloalkyl" denotes a saturated carbocyclic group, containing 3 to 7 carbon atoms. For example, a cycloalkyl group is cyclopropyl, cyclobutyl, cyclopentyl, cyclohexyl and cycloheptyl, and these groups may optionally be substituted by one or two $(C_1-C_4)$-alkyl substituents, for example methyl or ethyl.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. If possible, compounds of formula I may be converted into pharmaceutically salts. It should be understood that pharmaceutically acceptable salts are included in the present invention.

"Therapeutically effective amount" means an amount that is effective to prevent, alleviate or ameliorate symptoms of disease or prolong the survival of the subject being treated.

It is an object of the present invention to provide compounds having the following formula:

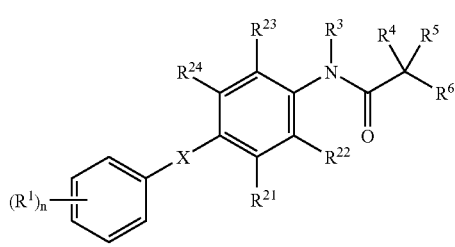

wherein
$R^1$ is halogen, halogen-$(C_1-C_6)$-alkyl, cyano, $(C_1-C_6)$-alkoxy or halogen-$(C_1-C_6)$-alkoxy;
$R^{21}$, $R^{22}$, $R^{23}$ and $R^{24}$ are each independently selected from the group consisting of hydrogen, $(C_1-C_6)$-alkyl, halogen, halogen-$(C_1-C_6)$-alkyl, hydroxy, $(C_1-C_6)$-alkoxy and —CHO;
$R^3$ is hydrogen or $(C_1-C_3)$-alkyl;
$R^4$, $R^5$ are each independently selected from the group consisting of hydrogen, $(C_1-C_6)$-alkyl, $(C_1-C_6)$-alkoxy or —COO$(C_1-C_6)$alkyl;
or, alternatively, $R^4$ and $R^5$, together with the C-atom to which they are attached, form a $(C_3-C_7)$-cycloalkyl ring;
$R^6$ is —CO—NR$^7$R$^8$; —COO$(C_1-C_6)$-alkyl, —CN, —N(R)$_2$ or —NHC(O)R;
$R^7$ and $R^8$ are each independently selected from the group consisting of hydrogen, $(C_1-C_6)$-alkyl, NH$_2$ or hydroxy;
R is hydrogen or $(C_1-C_6)$-alkyl;
n is 0, 1, 2 or 3;
X is —CHRO, —OCHR—, —CH$_2$S—, —SCH$_2$—, —CH$_2$CH$_2$—, —CH=CH— or —C≡C—;
or the pharmaceutically acceptable salts thereof.

Among compounds of the present invention certain compounds of formula I are preferred, for example the compounds of formula Ia below are preferred embodiments:

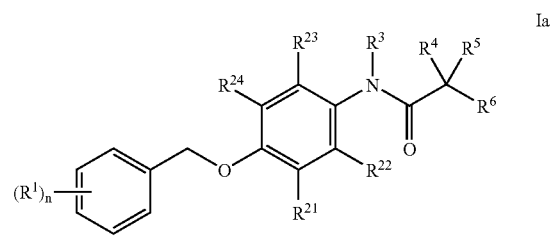

wherein
$R^1$ is halogen, halogen-$(C_1-C_6)$-alkyl, cyano, $(C_1-C_6)$-alkoxy or halogen-$(C_1-C_6)$-alkoxy;
$R^{21}$, $R^{22}$, $R^{23}$ and $R^{24}$ are each independently selected from the group consisting of hydrogen and halogen;
$R^3$ is hydrogen or $(C_1-C_3)$-alkyl;
$R^4$ is hydrogen or $(C_1-C_6)$-alkyl;
$R^5$ is hydrogen or $(C_1-C_6)$-alkyl;
or, alternatively, $R^4$ and $R^5$, together with the carbon atom to which they are attached, form a $(C_3-C_7)$-cycloalkyl ring;
$R^6$ is —CO—NR$^7$R$^8$, —COO$(C_1-C_6)$-alkyl, or —CN;
$R^7$ and $R^8$ are each independently hydrogen, methyl or ethyl; and
n is 1, 2 or 3;
or the pharmaceutically acceptable salts thereof.

In one embodiment of the invention, compounds of formula I wherein X is CH$_2$O or OCH$_2$ are preferred. For example, the invention provides compounds wherein X is CH$_2$O, preferably where X is CH$_2$O and $R^6$ is —COOC$_{(1-6)}$ alkyl. Preferred are further those compounds of formula I, wherein X is CH$_2$O, $R^1$ is fluorine or trifluoromethyl and $R^6$ is —COOCH$_3$, for example the following compounds:

N-[4-(3-fluoro-benzyloxy)-phenyl]-malonamic acid methyl ester,

N-[3-fluoro-4-(3-fluoro-benzyloxy)-phenyl]-malonamic acid methyl ester,

N-[4-(4-fluoro-benzyloxy)-phenyl]-malonamic acid methyl ester,

N-[2-fluoro-4-(3-fluoro-benzyloxy)-phenyl]-malonamic acid methyl ester,

N-[4-(2,4-difluoro-benzyloxy)-phenyl]-malonamic acid methyl ester,

N-[4-(2-fluoro-benzyloxy)-phenyl]-malonamic acid methyl ester,

N-[4-(2,4,5-trifluoro-benzyloxy)-phenyl]-malonamic acid methyl ester,

N-[2-fluoro-4-(4-fluoro-benzyloxy)-phenyl]-malonamic acid methyl ester,

N-[4-(3,5-bis-trifluoromethyl-benzyloxy)-2-fluoro-phenyl]-malonamic acid methyl ester,
N-[4-(3-fluoro-benzyloxy)-3-methyl-phenyl]-malonamic acid methyl ester or
N-[3-chloro-4-(3-fluoro-benzyloxy)-phenyl]-malonamic acid methyl ester.

Further preferred are compounds of formula I, wherein X is $CH_2O$ and $R^6$ is —$CONH_2$, for example the following compounds:
cyclopropane-1,1-dicarboxylic acid amide [4-(3-fluoro-benzyloxy)-phenyl]-amide,
N-[4-(3-fluoro-benzyloxy)-phenyl]-malonamide,
N-[4-(3-fluoro-benzyloxy)-phenyl]-2-methyl-malonamide,
N-[3-fluoro-4-(3-fluoro-benzyloxy)-phenyl]-malonamide,
N-[4-(4-fluoro-benzyloxy)-phenyl]-malonamide,
N-[4-(2,4-difluoro-benzyloxy)-phenyl]-malonamide,
N-[4-(2,4,5-trifluoro-benzyloxy)-phenyl]-malonamide,
N-[4-(2-fluoro-benzyloxy)-phenyl]-malonamide,
N-(4-benzyloxy-phenyl)-malonamide,
N-[4-(4-chloro-benzyloxy)-phenyl]-malonamide,
N-[4-(3-fluoro-benzyloxy)-2-hydroxy-phenyl]-malonamide,
N-[2-fluoro-4-(4-fluoro-benzyloxy)-phenyl]-malonamide,
N-[4-(3-fluoro-benzyloxy)-3-methyl-phenyl]-malonamide,
N-[3-chloro-4-(3-fluoro-benzyloxy)-phenyl]-malonamide or
cyclopropane-1,1-dicarboxylic acid amide [2-fluoro-4-(4-fluoro-benzyloxy)-phenyl]-amide.

Preferred are compounds of formula I wherein X is —$OCH_2$—, for example, compounds where X is —$OCH_2$— and $R^6$ is —$NHCOCH_3$ or —NHCOH. Examples of such compounds are the following:
2-Acetylamino-N-[2-fluoro-4-(4-fluoro-benzyloxy)-phenyl]-acetamide,
2-Acetylamino-N-[2-fluoro-4-(3-fluoro-benzyloxy)-phenyl]-acetamide,
N-[2-Fluoro-4-(4-fluoro-benzyloxy)-phenyl]-2-formylamino-acetamide or
N-[2-Fluoro-4-(3-fluoro-benzyloxy)-phenyl]-2-formylamino-acetamide.

Also preferred are compounds of formula I wherein X is —$OCH_2$— and $R^6$ is —$NH_2$.

The following compound is an example thereof:
2-amino-N-[2-fluoro-4-(4-fluoro-benzyloxy)-phenyl]-acetamide.

In another embodiment, the invention provides compounds of formula I wherein X is —$CH_2CH_2$—, —CH=CH—, or —C≢C—. Such compounds include those in which X is —CH=CH—. Another preferred group of compounds of formula I are those, wherein X is —CH=CH— and $R^6$ is —$COOCH_3$ or —$CONH_2$, for example the following:
N-{4-[2-(4-fluoro-phenyl)-vinyl]-phenyl}-malonamic acid methyl ester,
N-{4-[2-(3-fluoro-phenyl)-vinyl]-phenyl}-malonamide,
N-{4-[2-(4-fluoro-phenyl)-vinyl]-phenyl}-malonamide or
N-{4-[2-(3-fluoro-phenyl)-vinyl]-phenyl}-malonamic acid methyl ester.

In yet another emobidment, the invention provides compounds of formula I in which X is —$CH_2S$— or —$SCH_2$—. For example, such preferred compounds include those in which X is $SCH_2$ and $R^6$ is $COOCH_3$ or $CONH_2$. Examples of such compounds are the following:
N-[4-(3-fluoro-benzylsulfanyl)-phenyl]-malonamic acid methyl ester;
and N-[4-(3-fluoro-benzylsulfanyl)-phenyl]-malonamide.

In a further embodiment, the invention provides compounds of formula I in which $R^1$ is a halogen or halogen-(C1–C6)-alkyl. Among these compounds, those having one or more fluorine or trifluoromethyl group are preferred. Also preferred are compounds in which $R^1$ is hydrogen, methyl, or methoxy. Examples of such compounds are the following:
N-(4-benzyloxy-phenyl)-malonamide,
N-(4-benzyloxy-phenyl)-malonamic acid methyl ester; and
N-{4-[2-(4-methoxy-phenyl)-vinyl]-phenyl}-malonamic acid methyl ester; and In one embodiment, preferred compounds of the invention further include those in which $R^6$ is COO(C1–C6)alkyl, for example, compounds in which $R^6$ is $COOCH_3$. Examples of such compounds are the following:
N-[4-(3-fluoro-benzyloxy)-phenyl]-malonamic acid methyl ester;
N-[4-(3-fluoro-benzyloxy)-phenyl]-2-methyl-malonamic acid methyl ester;
N-[4-(3-fluoro-benzyloxy)-phenyl]-2-methoxy-malonamic acid methyl ester;
N-[4-(3-fluoro-benzyloxy)-phenyl]-N-methyl-malonamic acid methyl ester;
N-[4-(3-fluoro-benzyloxy)-2-trifluoromethyl-phenyl]-malonamic acid methyl ester;
N-[4-(4-trifluoromethyl-benzyloxy)-phenyl]-malonamic acid methyl ester;
N-[2-fluoro-4-(4-fluoro-benzyloxy)-phenyl]-malonamic acid ethyl ester;
N-[2-fluoro-4-(4-trifluoromethyl-benzyloxy)-phenyl]-malonamic acid methyl ester;
N-[4-(3-fluoro-benzyloxy)-3-formyl-phenyl]-malonamic acid methyl ester;
N-[4-(3-fluoro-benzyloxy)-3-methoxy-phenyl]-malonamic acid methyl ester;
N-{4-[2-(3-fluoro-phenyl)-vinyl]-phenyl}-malonamic acid methyl ester;
N-{4-[2-(4-fluoro-phenyl)-vinyl]-phenyl}-malonamic acid methyl ester;
N-(4-benzyloxy-phenyl)-malonamic acid methyl ester;
N-[4-(3-fluoro-phenoxymethyl)-phenyl]-malonamic acid methyl ester; and
N-[4-(3-fluoro-benzylsulfanyl)-phenyl]-malonamic acid methyl ester.

In another embodiment, the invention provides compounds in which $R^6$ is $CONR^7R^8$, for example, compounds where $R^6$ is $CONH_2$. Examples of such compounds are the following:
cyclopropane-1,1-dicarboxylic acid amide [4-(3-fluoro-benzyloxy)-phenyl]-amide;
N-[4-(3-fluoro-benzyloxy)-phenyl]-malonamide;
N-[4-(3-fluoro-benzyloxy)-phenyl]-2-methyl-malonamide;
N-[4-(3-fluoro-benzyloxy)-phenyl]-2,2-dimethyl-malonamide;
N-[4-(4-fluoro-benzyloxy)-phenyl]-malonamide;
N-[4-(4-trifluoromethyl-benzyloxy)-phenyl]-malonamide;
N-{4-[2-(3-fluoro-phenyl)-vinyl]-phenyl}-malonamide;
N-{4-[2-(4-fluoro-phenyl)-vinyl]-phenyl}-malonamide;
N-[2-fluoro-4-(3-fluoro-benzyloxy)-phenyl]-malonamide;

In yet another embodiment, the invention provides compounds in which $R^6$ is NHCOR. For example, preferred compounds are those in which $R^6$ is $NHCOCH_3$ or NHCOH.

Examples of such compounds are the following:

2-acetylamino-N-[2-fluoro-4-(4-fluoro-benzyloxy)-phenyl]-acetamide;

2-acetylamino-N-[2-fluoro-4-(3-fluoro-benzyloxy)-phenyl]-acetamide;

N-[2-fluoro-4-(4-fluoro-benzyloxy)-phenyl]-2-formylamino-acetamide;

N-[2-fluoro-4-(3-fluoro-benzyloxy)-phenyl]-2-formylamino-acetamide; and 2-amino-N-[2-fluoro-4-(4-fluoro-benzyloxy)-phenyl]-acetamide.

In a further embodiment, the invention provides compounds in which $R^6$ is $N(R)_2$, particularly those compounds in which $R^6$ is $NH_2$.

The invention also provides compounds in which $R^6$ is CN. An example of such a compound is 2-cyano-N-[4-(3-fluoro-benzyloxy)-phenyl]-acetamide.

The compounds of the invention, such as those of formula I, can be manufactured by reacting a compound of formula:

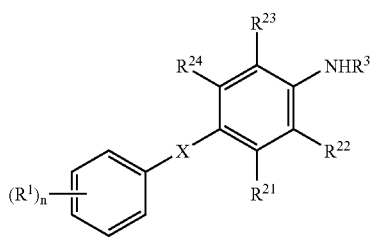

II with a compound of formula:

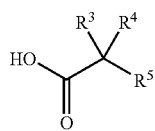

III to obtain a compound of formula:

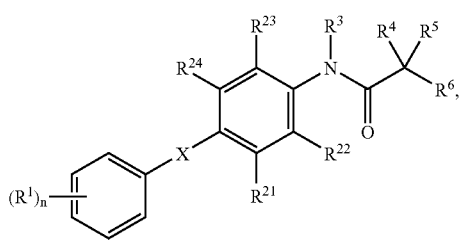

I and, optionally, converting a compound of formula I into a pharmaceutically acceptable salt.

In accordance with the present invention, a possibility to prepare compounds of formula I is shown in scheme 1: The key intermediates A are accessible through nucleophilic substitution of aromatic nitro compounds containing p-substituted leaving groups with benzylic alcohols or thiols. P-substituted leaving groups can be for example halogens (F, Cl, Br, I), tosylates, mesylates or triflates. These substitution reactions can be conducted neat or in inert solvents like for example toluene or xylene. Preferred reaction temperatures are between 50° and 150° C. Alternatively, compounds A can be prepared by Williamson-ether synthesis, starting from p-nitrophenols and benzylic halides, tosylates, mesylates or triflates. Bases used can be for example alcoholates or carbonates (sodium, potassium or cesium carbonate). Preferred solvents are lower alcohols, acetonitrile or lower ketones at temperatures between 20° C. and reflux temperature. Another approach is the Mitsunobu-coupling of benzylic alcohols with p-nitrophenols. The reaction is done as usual in inert solvents like for example diethyl ether or tetrahydrofuran, using dialkyl-azo-dicarboxylates in presence of phosphines (for example tributyl- or triphenyl-phosphine).

The key intermediates A are reduced to the amino-compounds B using catalytic hydrogenation (for example Platinum on charcoal in lower alcohols, ethyl acetate or tetrahydrofurane). An alternative is the reduction of the nitro-group by metals like iron, tin, or zinc in acidic media like diluted hydrochloric acid or acetic acid. Metals can also be replaced by metal salts (for example tin-(II)-chloride).

Intermediates B can be acylated by known methods to give the desired compounds I-A. These reactions can be done with acid chlorides and bases (for example trialkylamines, sodium carbonate or potassium carbonate, sodium hydrogen carbonate or potassium hydrogen carbonate), eventually in presence of an acylation catalyst (e.g. 1 to 10 mol % of N,N-dimethyl-4-aminopyridine) in solvents like dichloromethane, ethyl acetate or acetonitrile, preferentially at room temperature. An alternative is the well known coupling of an acid with the amine B using coupling reagents like N,N'-dicyclohexylcarbodiimide (DCC), N-(3-dimethylaminopropyl)-N'-ethyl-carbodiimide hydrochloride (EDC) or 1,1'-carbonyl-diimidazole (CDI) in solvents like dichloromethane, diethyl ether or THF, preferentially at 0 to 40° C. Intermediates B can also primarily be monoalkylated by known methods (see for example Johnstone et al, *J. Chem. Soc.* (*C*). 1969, 2233 or Krishnamurthy et al., *Tetrahedron Lett.* 1982, 23, 3315) to give compounds D. These are then acylated as previously described to lead to the desired compounds I-B.

Compounds with inverted ether or thioether linkers can be obtained by similar reactions, as depicted in scheme 1a. The key-intermediates A' are then further transformed into the final products by the reaction sequences already mentioned in scheme 1.

Additional functional group manipulations can be done by standard methods on the acylated compounds to obtain all compounds of formula I (for example: functionalising the malonic position by deprotonation and reaction with electrophiles).

Scheme 1
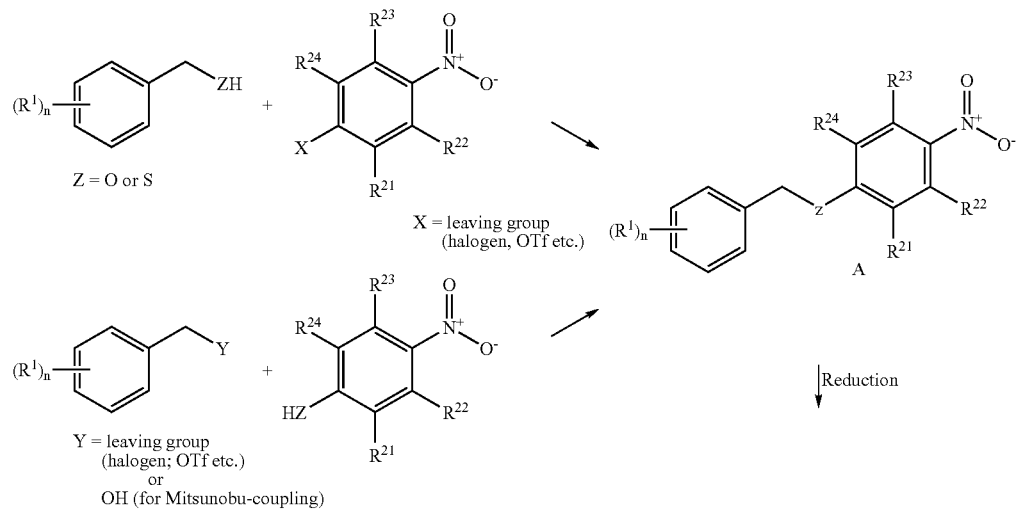
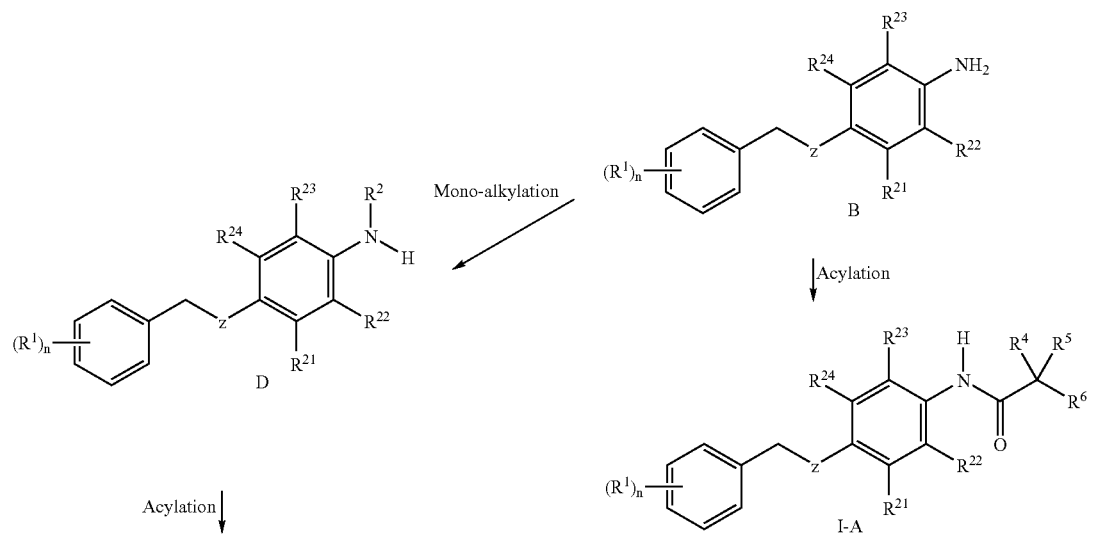
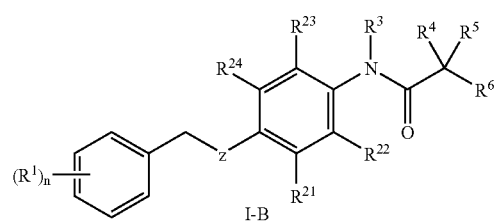

Scheme 1a

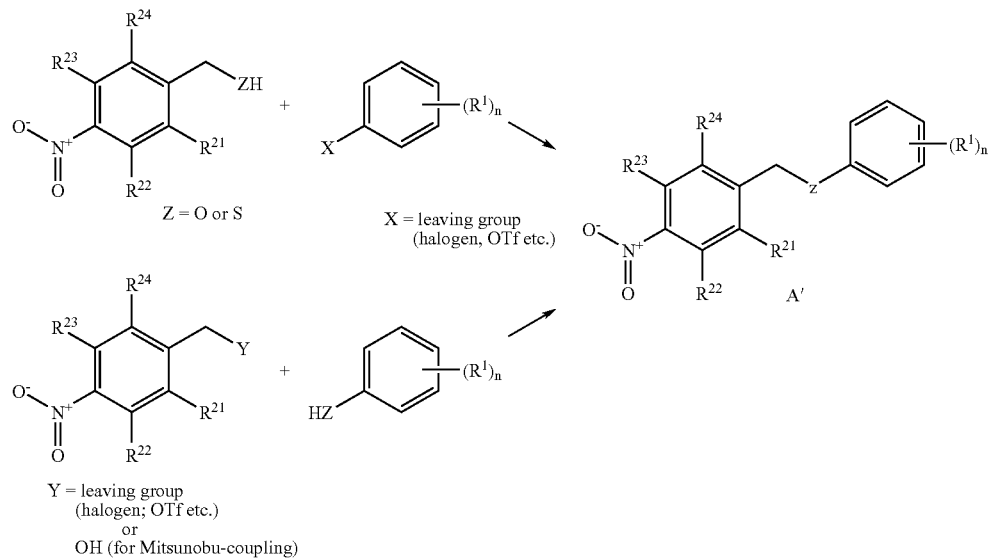

Alternatively, in accordance with the present invention, compounds B can also be prepared by alkylation of N-protected p-hydroxyanilines with benzylic halides or by Mitsunobu-coupling of N-protected p-hydroxyanilines with benzylic alcohols (scheme 2) by the methods described previously. Protective groups PG can be for example N-Boc (N-tert.-butoxycarbonyl) or N-acetyl. Deprotection of F leads to the intermediates B.

Obviously, compounds with inverted ether and thioether linkers can be prepared by similar reaction sequences, inverting substituent-patterns on the aromatic moieties.

Scheme 2

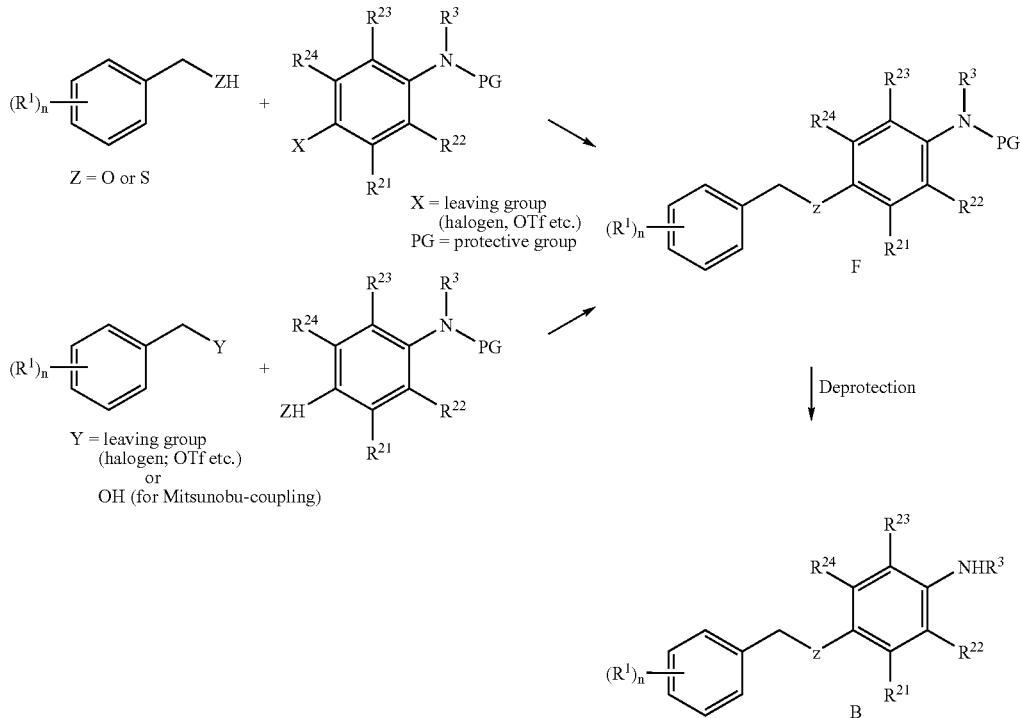

Another method to prepare compounds of the type D or I-B involves cross-coupling reactions of arylstannanes (Lam et al., *Tetrahedron Lett.* 2002, 43, 3091), arylboronates (Lam et al., *Synlett* 2000, 5, 674); Chan et al., Tetrahedron Lett. 1998, 39, 2933) or aryl halides (Buchwald et al., *J. Amer. Chem. Soc.* 1996, 118, 7215) with the corresponding amines or amides (scheme 3).

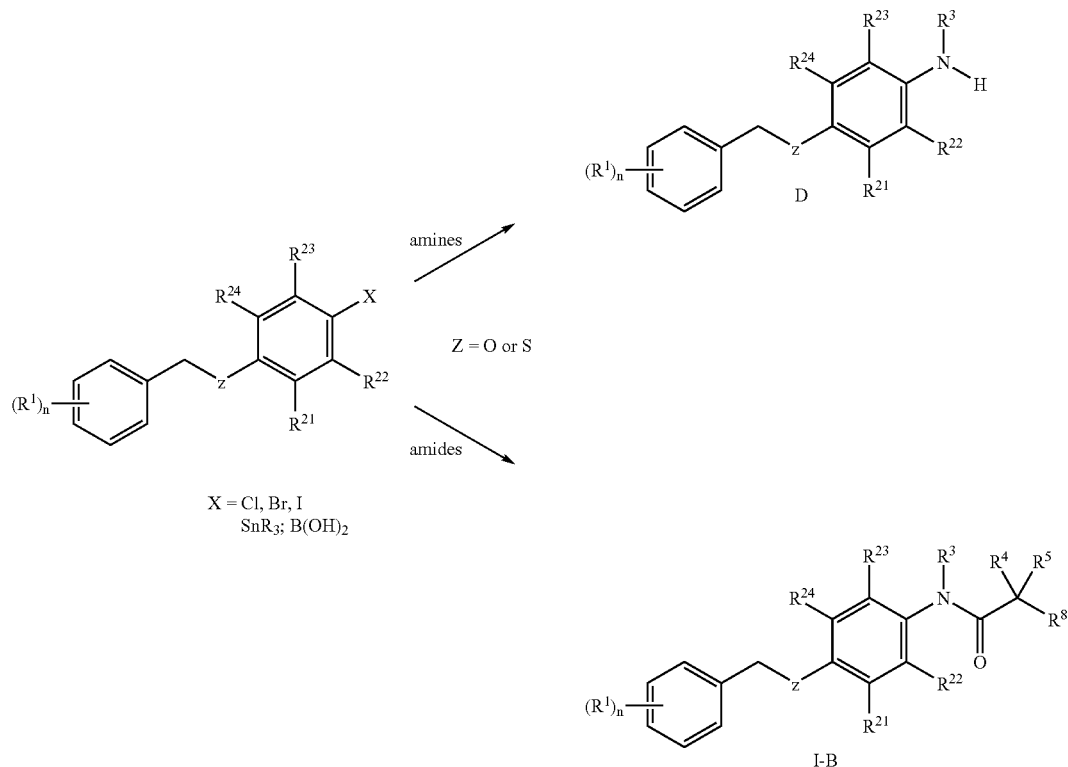

Scheme 3

Once again, compounds with inverted ether and thioether linkers can be prepared by similar reaction sequences, inverting substituent-patterns on the aromatic moieties.

A possibility to prepare compounds I where X is —$CH_2CH_2$— or —CH=CH— is shown in scheme 4. Wittig- or Wittig-Horner reactions between phosphor-ylides and aromatic aldehydes under standard conditions leads to styrene-derivatives G. These intermediates can be reduced to intermediates H or J Usually, reduction of G by Bechamp-type conditions leads to compounds H, which can then be further reduced to compounds J by catalytic hydrogenation. Using harsher hydrogenation conditions, compounds G can be reduced in one step to give compound J. Compounds H or J are then further processed by the methods depicted in scheme 1 to yield the final products I. Another method to prepare compounds of the type G involves nitration of styrene-derivatives.

Scheme 4

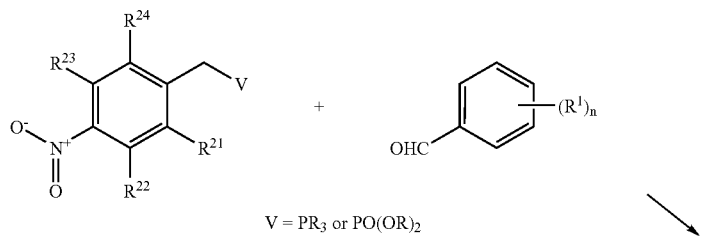

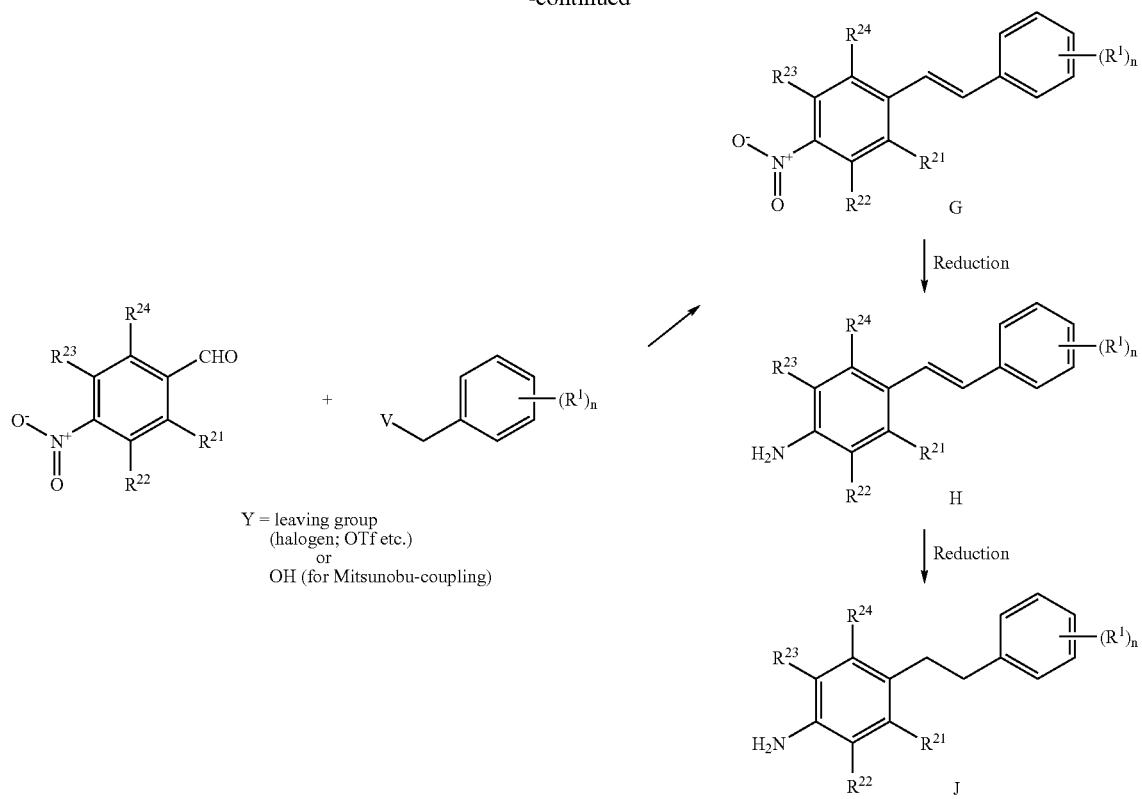

The compounds of the invention are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (G. M. Sullivan, International patent application No. WO 01/34172 A2), peripheral neuropathy caused by cancer chemotherapy (G. Bobotas, International Patent Application No. WO 97/33572 A1), or the treatment of multiple sclerosis (R. Y. Harris, International patent application No. WO 96/40095 A1) and other neuroinflammatory diseases.

The compounds of the invention are especially useful for the treatment and prevention of Alzheimer's disease and senile dementia.

The pharmacological activity of the compounds was tested using the following method:

The cDNA's encoding human MAO-A and MAO-B were transiently transfected into EBNA cells using the procedure described by E.-J. Schlaeger and K. Christensen (Transient Gene Expression in Mammalian Cells Grown in Serum-free Suspension Culture; Cytotechnology, 15: 1–13, 1998). After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophometric assay adapted from the method described by M. Zhou and N. Panchuk-Voloshina (A One-Step Fluorometric Method for the Continuous Measurement of Monoamine Oxidase Activity, Analytical Biochemistry, 253: 169–174, 1997). Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horseradish peroxidase (Roche Biochemicals) and 80 μM N-acetyl-3,7,-dihydroxyphenoxazine (Amplex Red, Molecular Probes). The samples were further incubated for 30 min at 37° C. in a final volume of 200 μl and absorbance was then determine at a wavelength of 570 nm using a SpectraMax plate reader (Molecular Devices). Background (non-specific) absorbance was determined in the presence of 10 μM clorgyline for MAO-A or 10 μM L-deprenyl for MAO-B.

$IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of preferred compounds of the invention as measured in the assay described above are in the range of 1000 nM or less, typically 100 nM or less, and ideally 50 nM or less.

In the table below are disclosed some $IC_{50}$ values (nM) of preferred compounds.

| Example No. | $IC_{50}$ (nM) |
| --- | --- |
| 1 | 11 |
| 2 | 7.9 |
| 3 | 10.9 |
| 6 | 13 |
| 8 | 9.6 |
| 9 | 7.2 |
| 10 | 11.2 |
| 11 | 7.5 |
| 14 | 9 |
| 25 | 11 |
| 27 | 11 |
| 28 | 8 |
| 29 | 8 |
| 34 | 18 |
| 38 | 16 |
| 39 | 5 |
| 40 | 15 |
| 41 | 13 |
| 44 | 9 |
| 47 | 14 |
| 48 | 19 |
| 49 | 10 |
| 50 | 6 |
| 56 | 10 |
| 57 | 18 |
| 66 | 16 |
| 70 | 11 |
| 72 | 7 |
| 75 | 13 |
| 76 | 16 |

The compounds of the invention can be formulated into pharmaceutical compositions. The pharmaceutical compositions can be administered orally, e.g. in the form of tablets, coated tablets, dragées, hard and soft gelatine capsules, solutions, emulsions or suspensions. The pharmaceutical compositions also can be administered rectally, e.g. in the form of suppositories, or parenterally, e.g. in the form of injection solutions.

The compounds of the invention can be processed with pharmaceutically acceptable carriers, e.g. inert, inorganic or organic carriers, such as those generally used in the formulation of pharmaceutical compositions. Such pharmaceutically acceptable carriers are provided, for example, in *Remington: The Science and Practice of Pharmacy* (Mack Publishing, 1995). Lactose, corn starch or derivatives thereof, talc, stearic acid or its salts and the like can be used, for example, as such carriers for tablets, coated tablets, dragees and hard gelatine capsules.

Suitable carriers for soft gelatine capsules are, for example, vegetable oils, waxes, fats, semi-solid and liquid polyols and the like; depending on the nature of the active substance no carriers are, however, usually required in the case of soft gelatine capsules.

Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of the compounds of the invention, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the present invention are selective MAO-B inhibitors. Thus, in another embodiment, the present invention provides for methods of treating diseases that are mediated by monoamine oxidase B. Such methods include administering a therapeutically effective amount of a compound of the invention, for example, a compound of formula I or a pharmaceutically acceptable salt thereof, to a patient in need of such treatment. In a preferred embodiment, the invention provides a method for the treatment of Alzheimer's diease. In another preferred embodiment, the present invention provides a method for the treatment of senile demenita.

The dosage at which a compound of the invention is administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof. Unless otherwise indicated, the following examples have been performed, regardless of the tense in which they are written.

EXAMPLE 1

N-[4-(3-Fluoro-benzyloxy)-phenyl]-malonamic acid methyl ester a) 1-(3-Fluorobenzyloxy)-4-nitro-benzene A mixture of 5.04 g (40 mmol) 3-fluorobenzyl alcohol and 1.29 g (4 mmol) tris-(dioxa-3,6-heptyl)amine is treated with 2.47 g (44 mmol) of potassium hydroxide. The mixture is stirred at room temperature for 10 min, then 5.55 g (44 mmol) of 4-fluoro-nitrobenzene is slowly added through a dropping funnel. The mixture is kept for 45 min at 80° C., cooled to room temperature and diluted with about 75 ml water. Extraction with ethyl acetate and washing with 2M aqueous hydrochloric acid yields a yellowish organic phase, which is dried and evaporated. The residue is recrystallised from methanol to give 6.07 g (61%) of the title compound. Yellow crystals, mp=104–105° C.

b) 4-(3-Fluoro-benzyloxy)-phenylamine 3 g (12.1 mmol) of 1-(3-fluorobenzyloxy)-4-nitro-benzene is dissolved in 125 ml of methanol. 150 mg of Pt 5% on charcoal is added and hydrogenation done under normal pressure for about 17 h. The catalyst is filtered and the solution evaporated to yield 2.51 g (95%) of crude brownish material. MS: m/e=218.4 (M$^+$+H).

c) N-[4-(3-Fluoro-benzyloxy)-phenyl]-malonamic acid methyl ester

A solution of 242 mg (1.77 mmol) chlorocarbonyl-acetic acid methyl ester in 2 ml dichloromethane is added dropwise to an ice-cooled solution of 350 mg (1.61 mmol) 4-(3-fluoro-benzyloxy)-phenylamine in 7 ml of pyridine. The mixture is then stirred for 2 h at room temperature, diluted with water, acidified with dil. hydrochloric acid and extracted with ethyl acetate. The organic phase is dried. Chromatography (silica gel, ethyl acetate/hexane 1:1) yields 99 mg (19%) of the title compound. Yellowish solid; MS: m/e=418.1 (M$^+$+H).

EXAMPLE 2

Cyclopropane-1,1-dicarboxylic acid amide [4-(3-fluoro-benzyloxy)-phenyl]-amide

A solution of 126 mg (1 mmol) of 1-(aminocarbonyl)-1-cyclopropan-carboxylic acid and of 212 mg (1 mmol) 4-(3-fluoro-benzyloxy)-phenylamine (prepared as in example 1b) in 10 ml dichloromethane is cooled to 0° C. and treated with 206 mg (1.1 mmol) N-(–3-dimethylaminopropyl)-N'-ethyl-carbodiimide-hydrochloride (EDCI). The mixture is stirred for additional 2 h at room temperature, evaporated and acidified with dil. citric acid. Extraction with ethyl acetate and recrystallisation from methanol yields 178 mg (56%) of the title compound. Yellowish solid; MS: m/e=329.3 (M$^+$+H).

EXAMPLE 3

N-[4-(3-Fluoro-benzyloxy)-phenyl]-malonamide 99 mg (0.31 mmol) N-[4-(3-fluoro-benzyloxy)-phenyl]-malonamic acid methyl ester (example 1) is dissolved in a mixture of 0.5 ml tetrahydrofuran and 1.0 ml of aqueous ammonium hydroxide (25%). The reaction vessel is capped and kept at 60° C. for 2.5 h. The reaction mixture is cooled, evaporated to dryness and diluted with water. Filtration provides 48 mg (51%) of the title compound as a light yellow solid. MS: m/e=303.2 (M$^+$+H).

EXAMPLE 4

2-Cyano-N-[4-(3-fluoro-benzyloxy)-phenyl]-acetamide

The title compound is prepared in analogy to example 2, starting from 4-(3-fluoro-benzyloxy)-phenylamine (prepared as in example 1b) and cyanoacetic acid. Yield after recrystallisation from methanol: 50%. Colorless crystals with mp=164–166° C.

EXAMPLE 5

N-[4-(3-Fluoro-benzyloxy)-phenyl]-2-methyl-malonamic acid methyl ester

The title compound is prepared in analogy to example 2, starting from 4-(3-fluoro-benzyloxy)-phenylamine (as prepared in example 1b) and 2-methyl-malonic acid monomethyl ester (Nader et al., *Chem. Ber.* 1986, 119, 1196). Yield after flash-chromatography with dichloromethane/methanol 98:2: 40%. Colorless solid. Mp=119° C.

EXAMPLE 6

N-[4-(3-Fluoro-benzyloxy)-phenyl]-2-methyl-malonamide

The title compound is prepared in analogy to example 3 from N-[4-(3-fluoro-benzyloxy)-phenyl]-2-methyl-malonamic acid methyl ester and ammonium hydroxide. Colorless solid. Mp=206° C.

EXAMPLE 7

N-[4-(3-Fluoro-benzyloxy)-phenyl]-2,2-dimethyl-malonamide a) N-[4-(3-Fluoro-benzyloxy)-phenyl]-2,2-dimethyl-malonamic acid ethyl ester The title compound is prepared in analogy to example 2, starting from 4-(3-fluoro-benzyloxy)-phenylamine and 2,2-dimethyl-malonic acid monoethyl ester (Holmes et al., *J. Amer. Chem. Soc.* 1984, 106, 2353). Yield after flash-chromatography with cyclohexane/ethyl acetate 7:3: 79%. Colorless oil. MS: m/e=359 (M$^+$).

b) N-[4-(3-Fluoro-benzyloxy)-phenyl]-2,2-dimethyl-malonamide

The title compound is prepared in analogy to example 3 from N-[4-(3-fluoro-benzyloxy)-phenyl]-2,2-dimethyl-malonamic acid ethyl ester and ammonium hydroxide. Colorless solid. MS: m/e=331.4 (M$^+$+H).

EXAMPLE 8

N-[3-Fluoro-4-(3-fluoro-benzyloxy)-phenyl]-malonamic acid methyl ester a) 3-Fluoro-4-(3-fluoro-benzyloxy)-nitrobenzene

A mixture of 10.0 g (64 mmol) 2-fluoro-4-nitrophenol, 13.24 g (70 mmol) 3-fluorobenzyl bromide and 17.6 g (127 mmol) potassium carbonate in 200 ml methyl-ethylketone is heated overnight at 80°. Water is added and the product is extracted with ethyl acetate, dried and evaporated. Recrystallisation from diethyl ether/hexane yields 12.68 g (75%) of a slightly yellow solid. MS: m/e=265.1 (M$^+$).

b) 3-Fluoro-4-(3-fluoro-benzyloxy)-phenylamine 12.68 g (47.8 mmol) of 3-fluoro-4-(3-fluoro-benzyloxy)-nitrobenzene in 150 ml ethyl acetate is treated with 1.27 g of 5% platinum on charcoal and hydrogenated for 6 h at room temperature and normal pressure. The catalyst is filtered and the solution evaporated to yield 11.03 g (98%) of dark brown oil. MS: m/e=235.1 (M$^+$).

c) N-[3-Fluoro-4-(3-fluoro-benzyloxy)-phenyl]-malonamic acid methyl ester

The title compound is prepared in analogy to example 1 from 3-fluoro-4-(3-fluoro-benzyloxy)-phenylamine and chlorocarbonyl-acetic acid methyl ester. Yield: 65%. Light yellow solid. MS: m/e=336.2 (M$^+$+H).

EXAMPLE 9

N-[3-Fluoro-4-(3-fluoro-benzyloxy)-phenyl]-malonamide

The title compound is prepared in analogy to example 3 from N-[3-fluoro-4-(3-fluoro-benzyloxy)-phenyl]-malonamic acid methyl ester and ammonium hydroxide. Light yellow solid. MS: m/e=321.2 (M$^+$+H).

EXAMPLE 10

N-[4-(4-Fluoro-benzyloxy)-phenyl]-malonamic acid methyl ester a) 4-(4-Fluoro-benzyloxy)-nitrobenzene The title compound is prepared in analogy to 1-(3-fluorobenzyloxy)-4-nitro-benzene, starting from 4-fluoro nitrobenzene and 4-fluoro benzyl alcohol. Yield: 86% of a slightly yellow solid. Mp.=124–126°.

b) 4-(4-Fluoro-benzyloxy)-phenylamine

Prepared in analogy to 4-(3-fluoro-benzyloxy)-phenylamine, by hydrogenation of 4-(4-fluoro-benzyloxy)-nitrobenzene. Yield: 100% of a slightly red solid. MS: m/e=218.2 (M$^+$+H).

c) N-[4-(4-Fluoro-benzyloxy)-phenyl]-malonamic acid methyl ester

The title compound is prepared in analogy to example 1 from 4-(4-fluoro-benzyloxy)-phenylamine and chlorocarbonyl-acetic acid methyl ester. Yield: 75%. Colorless solid. MS: m/e=318.2 (M$^+$+H).

EXAMPLE 11

N-[4-(4-Fluoro-benzyloxy)-phenyl]-malonamide

The title compound is prepared in analogy to example 3 from N-[4-(4-fluoro-benzyloxy)-phenyl]-malonamic acid methyl ester and ammonium hydroxide. Yield: 80%. Colorless solid. MS: m/e=303.2 (M$^+$+H).

EXAMPLE 12

N-[4-(4-Trifluoromethyl-benzyloxy)-phenyl]-malonamic acid methyl ester a) 4-(4-Trifluoromethyl-benzyloxy)-nitrobenzene Prepared in analogy to 1-(3-fluorobenzyloxy)-4-nitro-benzene, starting from 4-fluoro nitrobenzene and 4-trifluoromethyl benzyl alcohol. Yield after recristallisation from methanol: 82% of a brownish solid. Mp=80.5–81.5° C.

b) 4-(4-Trifluoromethyl-benzyloxy)-phenylamine

Prepared in analogy to 4-(3-fluoro-benzyloxy)-phenylamine, by hydrogenation of 4-(4-trifluoromethyl-benzyloxy)-nitrobenzene. Yield: 98% of a slightly yellow solid. MS: m/e=268.3 (M$^+$+H).

c) N-[4-(4-Trifluoromethyl-benzyloxy)-phenyl]-malonamic acid methyl ester

In analogy to example 1, the title compound is prepared from 4-(4-trifluoromethyl-benzyloxy)-phenylamine and chlorocarbonyl-acetic acid methyl ester. Yield: 71%. Colorless solid. MS: m/e=368.1 (M$^+$+H).

EXAMPLE 13

N-[4-(4-Trifluoromethyl-benzyloxy)-phenyl]-malonamide

The title compound is prepared in analogy to example 3 from N-[4-(4-trifluoromethyl-benzyloxy)-phenyl]-malonamic acid methyl ester and ammonium hydroxide. Yield=65%. Colorless solid. MS: m/e=353.1 (M$^+$+H).

EXAMPLE 14

N-[2-Fluoro-4-(3-fluoro-benzyloxy)-phenyl]-malonamic acid methyl ester a) 2-Fluoro-4-(3-fluoro-benzyloxy)-nitrobenzene Prepared in analogy to 3-fluoro-4-(3-fluoro-benzyloxy)-nitrobenzene, starting from 3-fluoro-4-nitrophenol and 3-fluorobenzyl bromide. Yield after recrystallisation from diethyl ether/hexane: 100% of a white solid. MS: m/e=265.0 (M$^+$).

b) 2-Fluoro-4-(3-fluoro-benzyloxy)-phenylamine

The title compound is prepared in analogy to 3-fluoro-4-(3-fluoro-benzyloxy)-phenylamine by hydrogenation of 2-Fluoro-4-(3-fluoro-benzyloxy)-nitrobenzene. Yield: 98% of a dark brown oil. MS: m/e=235.0 (M$^+$).

c) N-[2-Fluoro-4-(3-fluoro-benzyloxy)-phenyl]-malonamic acid methyl ester

In analogy to example 1, the title compound is prepared from 2-fluoro-4-(3-fluoro-benzyloxy)-phenylamine and chlorocarbonyl-acetic acid methyl ester. Yield: 47%. Brownish solid. MS: m/e=336.1 (M$^+$+H).

EXAMPLE 15

N-[2-Fluoro-4-(3-fluoro-benzyloxy)-phenyl]-malonamide

The title compound is prepared in analogy to example 3 from N-[2-fluoro-4-(3-fluoro-benzyloxy)-phenyl]-malonamic acid methyl ester and ammonium hydroxide. Yield=87%. Slightly yellow solid. MS: m/e=321.3 (M$^+$+H).

EXAMPLE 16

N-[4-(3-Fluoro-phenoxymethyl)-phenyl]-malonamic acid methyl ester a)-Nitro-4-(3-fluoro-phenoxymethyl)-benzene A solution of 2.0 g (13 mmol) 4-nitrobenzyl alcohol and 3.60 g (13.7 mmol) triphenylphosphine in 30 ml tetrahydrofurane is treated with 1.54 g (13.7 mmol) of 3-fluorophenol. The mixture is cooled in an ice-bath and 2.39 g (13.7 mmol) of diethyl-aza-dicarboxylate is slowly added. The ice-bath is removed and the reaction mixture stirred over night at room temperature. The tetrahydrofuran is evaporated, the oily residue triturated with diethyl ether, filtered and concentrated. Chromatography (silica gel, ethyl acetate/hexane 1:9) yields 2.52 g (78%) of the title compound as a slightly yellow solid. MS: m/e=247.1 (M$^+$+H).

b) 4-(3-Fluoro-phenoxymethyl)-phenylamine g (4 mmol) of 1-Nitro-4-(3-fluoro-phenoxymethyl)-benzene in 40 ml methanol is treated with 0.25 g of 5% platinum on charcoal and hydrogenated for 1 h at room temperature and normal pressure. The catalyst is filtered and the solution evaporated to yield 0.98 g of the crude title compound as yellow oil. MS: m/e=218.3 ($M^+$+H).

c) N-[4-(3-Fluoro-phenoxymethyl)-phenyl]-malonamic acid methyl ester 211 mg (1 mmol) of the crude 4-(3-fluoro-phenoxymethyl)-phenylamine is dissolved in 3 ml dichloromethane. 110 mg (1.1 mmol) of triethylamine is added and the reaction mixture cooled in an ice-bath 132 mg (1 mmol) of methyl malonyl chloride is then added dropwise. The reaction mixture is stirred for additional 30 minutes in the ice-bath, then for 45 minutes at room temperature. The reaction mixture is treated with water, acidified with citric acid and extracted 3 times with dichloromethane. The organic phase is dried and evaporated. Chromatography (silica gel, ethyl acetate/hexane 1:1) yields 98 mg (32%) of the title compound as a colorless solid. MS: m/e=318.2 ($M^+$+H).

EXAMPLE 17

N-[4-(3-Fluoro-phenoxymethyl)-phenyl]-malonamide

The title compound is prepared in analogy to example 3 from N-[4-(3-Fluoro-phenoxymethyl)-phenyl]-malonamic acid methyl ester and and ammonium hydroxide. Yield=37%. Colorless solid. MS: m/e=303.2 ($M^+$+H).

EXAMPLE 18

Cyclopropane-1,1-dicarboxylic acid amide [4-(3-fluoro-phenoxymethyl)-phenyl]-amide The title compound is prepared in analogy to example 2 from 4-(3-Fluoro-phenoxymethyl)-phenylamine and 1-(aminocarbonyl)-1-cyclopropane-carboxylic acid. Yield=42%. Colorless solid. MS: m/e=329.3 ($M^+$+H).

EXAMPLE 19

N-[4-(3-Fluoro-benzyloxy)-phenyl]-2-methoxy-malonamic acid methyl ester

The title compound is prepared in analogy to example 2 from 4-(3-Fluoro-benzyloxy)-phenylamine and 2-methoxy-malonic acid monomethyl ester (Swan et al.; J. Chem. Soc. Perkin Trans. 1; 1985; 1757–1766). Yield=41%. Colorless solid. MS: m/e=348.2 ($M^+$+H).

EXAMPLE 20

N-[4-(3-Fluoro-benzyloxy)-2-trifluoromethyl-phenyl]-malonamic acid methyl ester a) 4-(3-Fluoro-benzyloxy)-1-nitro-2-trifluoromethyl-benzene Prepared in analogy to example 8 from 4-nitro-3-(trifluoromethyl)-phenol and 3-Fluoro-benzylbromide. Yield=85%. Yellowish solid. MS (ISP): m/e=333.2 ($M^+$+$NH_4$).

b) 4-(3-Fluoro-benzyloxy)-2-trifluoromethyl-phenylamine

Prepared in analogy to example 8b) by hydrogenation of 4-(3-Fluoro-benzyloxy)-1-nitro-2-trifluoromethyl-benzene. Yield=93%. Slightly yellow oil. MS: m/e=286.1 ($M^+$+H).

c) N-[4-(3-Fluoro-benzyloxy)-2-trifluoromethyl-phenyl]-malonamic acid methyl ester 0.515 g (1.8 mmol) 4-(3-Fluoro-benzyloxy)-2-trifluoromethyl-phenylamine is dissolved in 20 ml ethyl acetate. 0.38 g (4.51 mmol) sodium hydrogencarbonate is added and the mixture cooled in the ice-bath. 0.27 g (2.0 mmol) methyl malonyl chloride, dissolved in 5 ml ethyl acetate is slowly added over a period of about 15 min. The resulting mixture is stirred at room temperature overnight. 10 ml 2M aqueous hydrochloric acid is added, the organic layer separated and dried over magnesium sulfate. Evaporation of the solvent gives a slightly yellow solid which is recrystallised from methanol. Colorless solid, Yield=58%. MS: m/e=386.1 ($M^+$+H).

EXAMPLE 21

N-[2,5-Difluoro-4-(3-fluoro-benzyloxy)-phenyl]-malonamide a) 1,4-Difluoro-2-(3-fluoro-benzyloxy)-5-nitro-benzene Prepared in analogy to example 1a) from 2,4,5-trifluoronitrobenzene and 3-fluoro-benzyl alcohol. Colorless solid. Yield=55%. MS: m/e=283.1 ($M^+$).

b) 2,5-Difluoro-4-(3-fluoro-benzyloxy)-phenylamine

Prepared in analogy to example 8b) by hydrogenation of 1,4-difluoro-2-(3-fluoro-benzyloxy)-5-nitro-benzene. Yield=96%. Brown solid. MS: m/e=253.2 ($M^+$).

c) N-[2,5-Difluoro-4-(3-fluoro-benzyloxy)-phenyl]-malonamic acid methyl ester

Prepared in analogy to example 20c) from 2,5-difluoro-4-(3-fluoro-benzyloxy)-phenylamine and methyl malonyl chloride. Greyish solid. Yield=73%. MS: m/e=354.1 ($M^+$+H).

d) N-[2,5-Difluoro-4-(3-fluoro-benzyloxy)-phenyl]-malonamide

The title compound is prepared in analogy to example 3 from N-[2,5-difluoro-4-(3-fluoro-benzyloxy)-phenyl]-malonamic acid methyl ester and and ammonium hydroxide. Yield=56%. Colorless solid. MS: m/e=339.3 ($M^+$+H).

EXAMPLE 22

N-[4-(3-Fluoro-benzyloxy)-phenyl]-N-methyl-malonamic acid methyl ester a) [4-(3-Fluoro-benzyloxy)-phenyl]-methyl-amine 0.855 g (8.4 mmol) acetic anhydride is cooled to 0° and 0.475 g (10.3 mmol) acetic acid added dropwise. The reaction mixture is then heated to 55° for 2 hours. After cooling to room temperature the mixture is diluted with 0.5 ml dry tetrahydrofuran. A solution of 0.7 g (3.2 mmol) 4-(3-fluoro-benzyloxy)-phenylamine in 2 ml tetrahydrofuran is added dropwise at room temperature and the resulting mixture is stirred for 3 hours. Evaporation leaves a solid which is dissolved again in 2 ml tetrahydrofuran and cooled to 0°. 0.64 g (8.1 mmol) borane-methyl sulfide complex is slowly added under stirring and cooling. The mixture is stirred 1 h at 0° and 2 h at room temperature. After addition of 5 ml methanol, stirring is pursued for 1 h. The mixture is treated with 10 ml 1M aqueous hydrochloric acid and stirred overnight. The organic solvents are removed under vacuum and the aqueous phase adjusted to pH=10 bei addition of potassium carbonate. Extraction with diethyl ether, drying and evaporation yields 0.57 g (76%) of a colorless solid. MS: m/e=232.2 ($M^+$+H).

b) N-[4-(3-Fluoro-benzyloxy)-phenyl]-N-methyl-malonamic acid methyl ester

Prepared in analogy to example 20c) from [4-(3-fluoro-benzyloxy)-phenyl]-methyl-amine and methyl malonyl chloride. Yellowish oil. Yield=70%. MS: m/e=332.3 ($M^+$+H).

EXAMPLE 23

N-[4-(3-Fluoro-benzylsulfanyl)-phenyl]-malonamic acid methyl ester a) 1-Fluoro-3-(4-nitrophenylsulfanyl-methyl)-benzene Prepared in analogy to example 8 from 4-nitrothiophenol and 3-fluoro-benzylbromide. Yellowish solid. Yield=54%.

b) 4-(3-Fluoro-benzylsulfanyl)-phenylamine 1.75 g (6.7 mmol) 1-Fluoro-3-(4-nitrophenylsulfanylmethyl)-benzene and 5.55 g (100 mmol) of iron-powder are suspended in 35 ml water and 0.2 ml acetic acid. The mixture is heated overnight at 90°, then cooled and treated with saturated sodium carbonate solution. The suspension is filtered, the solid washed several times with ethyl acetate and the aqueous phase extracted 3 times with ethyl acetate. The combined organic phases are dried and evaporated to give 1.18 g (76%) of a yellowish waxy solid. MS: m/e=234.3 ($M^+$+H).

c) N-[4-(3-Fluoro-benzylsulfanyl)-phenyl]-malonamic acid methyl ester

Prepared in analogy to example 20c) from 4-(3-fluoro-benzylsulfanyl)-phenylamine and methyl malonyl chloride. Yellowish solid. Yield=64%. MS: m/e=334.2 ($M^+$+H).

EXAMPLE 24

N-[4-(3-Fluoro-benzylsulfanyl)-phenyl]-malonamide

Prepared in analogy to example 3 from N-[4-(3-fluoro-benzylsulfanyl)-phenyl]-malonamic acid methyl ester and ammonium hydroxide. Yield=47%. Colorless solid. MS: m/e=319.3 ($M^+$+H).

EXAMPLE 25

N-[4-(2,4-Difluoro-benzyloxy)-phenyl]-malonamic acid methyl ester a) 2,4-Difluoro-1-(4-nitro-phenoxymethyl)-benzene Prepared in analogy to example 8 from 4-nitrophenol and 2,4-difluoro-benzylbromide. Colorless solid. Yield=86%. MS: m/e=265.1 ($M^+$).

b) 4-(2,4-Difluoro-benzyloxy)-phenylamine

Prepared in analogy to example 8b) by hydrogenation of 2,4-difluoro-1-(4-nitro-phenoxymethyl)-benzene. Yield=99%. Brown solid. MS: m/e=235.1 ($M^+$).

c) N-[4-(2,4-Difluoro-benzyloxy)-phenyl]-malonamic acid methyl ester

Prepared in analogy to example 20c) from 4-(2,4-difluoro-benzyloxy)-phenylamine and methyl malonyl chloride. Colorless solid. Yield=99%. MS: m/e=336.2 ($M^+$+H).

EXAMPLE 26

N-[4-(2-Fluoro-benzyloxy)-phenyl]-malonamic acid methyl ester a) 1-Fluoro-2-(4-nitrophenoxy-methyl)-benzene Prepared in analogy to example 8 from 4-nitrophenol and 2-fluoro-benzylbromide. Colorless solid. Yield=74%. MS: m/e=247.1 ($M^+$).

b) 4-(2-Fluoro-benzyloxy)-phenylamine

Prepared in analogy to example 8b) by hydrogenation of 1-fluoro-2-(4-nitrophenoxy)-methyl-benzene. Yield=99%. Brown oil. MS: m/e=217.2 ($M^+$).

c) N-[4-(2-Fluoro-benzyloxy)-phenyl]-malonamic acid methyl ester

Prepared in analogy to example 20c) from 4-(2-fluoro-benzyloxy)-phenylamine and methyl malonyl chloride. Colorless solid. Yield=70%. MS: m/e=318.2 ($M^+$+H).

EXAMPLE 27

N-[4-(2,4,5-Trifluoro-benzyloxy)-phenyl]-malonamic acid methyl ester a) 1,2,4-Trifluoro-5-(4-nitro-phenoxymethyl)-benzene Prepared in analogy to example 8 from 4-nitrophenol and 2,4,5-trifluoro-benzylbromide. Colorless solid. Yield=92%. MS: m/e=283.0 ($M^+$).

b) 4-(2,4,5-Trifluoro-benzyloxy)-phenylamine

Prepared in analogy to example 8b) by hydrogenation 1,2,4-trifluoro-5-(4-nitro-phenoxymethyl)-benzene. Yield=97%. Slightly red solid. MS: m/e=254.1 ($M^+$+H).

c) N-[4-(2,4,5-Trifluoro-benzyloxy)-phenyl]-malonamic acid methyl ester

Prepared in analogy to example 20c) from 4-(2,4,5-trifluoro-benzyloxy)-phenylamine and methyl malonyl chloride. Colorless solid. Yield=91%. MS: m/e=352.2 ($M^+$−H).

EXAMPLE 28

N-[4-(2,4-Difluoro-benzyloxy)-phenyl]-malonamide

Prepared in analogy to example 3 from N-[4-(2,4-difluoro-benzyloxy)-phenyl]-malonamic acid methyl ester and ammonium hydroxide. Yield=49%. Colorless solid. MS: m/e=321.1 ($M^+$+H).

EXAMPLE 29

N-[4-(2,4,5-Trifluoro-benzyloxy)-phenyl]-malonamide

Prepared in analogy to example 3 from N-[4-(2,4,5-trifluoro-benzyloxy)-phenyl]-malonamic acid methyl ester and ammonium hydroxide. Yield=52%. Colorless solid. MS: m/e=339.2 ($M^+$+H).

EXAMPLE 30

N-[4-(2-Fluoro-benzyloxy)-phenyl]-malonamide

Prepared in analogy to example 3 from N-[4-(2-fluoro-benzyloxy)-phenyl]-malonamic acid methyl ester and ammonium hydroxide. Yield=30%. Colorless solid. MS: m/e=303.2 ($M^+$+H).

EXAMPLE 31

N-{4-[1-(3-Fluoro-phenyl)-ethoxy]-phenyl}-malonamide a) 1-Fluoro-3-(1-(4-nitrophenoxy)-ethyl)-benzene

Prepared in analogy to example 16a) from 1-(3-fluoro-phenyl)-ethanol (Balasubramanian et al., Synth. Commun., 1994, 24 (8), 1049) and 4-nitrophenol. Yellow oil. Yield=77%. MS: m/e=261.2 ($M^+$).

b) 4-[1-(3-Fluoro-phenyl)-ethoxy]-phenylamine

Prepared in analogy to example 8b) by hydrogenation of 1-fluoro-3-(1-(4-nitrophenoxy)-ethyl)-benzene. Yield=95%. Yellowish oil. MS: m/e=232.2 ($M^+$+H).

c) N-{4-[1-(3-Fluoro-phenyl)-ethoxy]-phenyl}-malonamic acid methyl ester

Prepared in analogy to example 20c) from 4-[1-(3-fluoro-phenyl)-ethoxy]-phenylamine and methyl malonyl chloride. Yellowish solid. Yield=30%. MS: m/e=332.4 ($M^+$+H).

d) N-{4-[1-(3-Fluoro-phenyl)-ethoxy]-phenyl}-malonamide

Prepared in analogy to example 3 from N-{4-[1-(3-fluoro-phenyl)-ethoxy]-phenyl}-malonamic acid methyl ester and ammonium hydroxide. Yield=55%. Colorless solid. MS: m/e=317.3 ($M^+$+H).

EXAMPLE 32

N-(4-Benzyloxy-phenyl)-malonamic acid methyl ester

Prepared in analogy to example 20c) from 4-benzyloxyaniline and methyl malonyl chloride. Yellowish solid. Yield=62%. MS: m/e=300.2 ($M^+$+H).

EXAMPLE 33

N-(4-Benzyloxy-phenyl)-malonamide

Prepared in analogy to example 3 from N-(4-benzyloxy-phenyl)-malonamic acid methyl ester and ammonium hydroxide. Yield=85%. Colorless solid. MS: m/e=285.1 ($M^+$+H).

EXAMPLE 34

N-[4-(4-Chloro-benzyloxy)-phenyl]-malonamide a) N-(4-Hydroxy-phenyl)-malonamide

A suspension of 6.0 g (18.5 mmol) of N-(4-benzyloxy-phenyl)-malonamide in 150 ml methanol is treated with 0.8 g of palladium 5% on charcoal. Hydrogenation is performed at room temperature and normal pressure overnight. The reaction mixture is then brought to reflux and filtered hot. Cooling of the filtrate yields 3.56 g (99%) of the title compound as a colorless solid. MS: m/e=285.1 ($M^+$+H).

b) N-[4-(4-Chloro-benzyloxy)-phenyl]-malonamide

Prepared in analogy to example 8 from N-(4-hydroxy-phenyl)-malonamide and 4-chloro-benzylbromide. Colorless solid. Yield=18%. MS: m/e=319.1 ($M^+$+H).

EXAMPLE 35

N-[4-(3-Fluoro-benzyloxy)-phenyl]-2-hydrazinocarbonyl-acetamide

A suspension of 0.35 g (1.1 mmol) of N-[4-(3-fluoro-benzyloxy)-phenyl]-malonamic acid methyl ester in 7 ml methanol is treated with 83 mg (1.7 mmol) of hydrazine hydrate. The reaction mixture is refluxed for 2 h, then another portion of 300 mg (6 mmol) of hydrazine hydrate is added and reflux is pursued for another 8 h. The mixture is cooled and hold overnight in the frig. The precipitate is filtered off and recrystallised from methanol to yield 0.043 g (12%) of filthy, colorless needles. MS: m/e=318.3 ($M^+$+H).

EXAMPLE 36

N-[4-(3-Fluoro-benzyloxy)-phenyl]-N'-hydroxy-malonamide

A solution of sodium methylate is prepared by dissolving 0.23 g (10 mmol) sodium in 10 ml methanol. This solution is cooled to 0° and 0.25 g (5 mmol) of hydroxylamine hydrochloride is added, followed by 0.317 g (1 mmol) of N-[4-(3-fluoro-benzyloxy)-phenyl]-malonamic acid methyl ester. The mixture is stirred for 2 h at room temperature, diluted with 25 ml of water and acidified to pH=3 by addition of citric acid. The precipitate is filtered and recrystallised from ethyl acetate, giving 0.123 mg (39%) of a colorless solid. MS: m/e=319.3 ($M^+$+H).

EXAMPLE 37

2-[4-(3-Fluoro-benzyloxy)-phenylcarbamoyl]-malonic acid dimethyl ester 0.15 g (0.47 mmol) of N-[4-(3-fluoro-benzyloxy)-phenyl]-malonamic acid methyl ester is dissolved in 7 ml tetrahydrofuran and cooled to 0°. 38 mg (1 mmol) of sodium hydride (55 to 65% in oil) is added and the mixture stirred for 45 minutes at room temperature. After cooling again to 0° a solution of 56 mg (0.6 mmol) methyl chloroformate in 0.5 ml tetrahydrofuran is slowly added with a seringe. The yellowish solution is stirred at room temperature for 2 h, treated with about 40 ml of water, acidified to pH=3 by addition of citric acid and extracted 3 times with ethyl acetate. The organic phase is dried over magnesium sulfate and concentrated in vacuo yielding 212 mg of a yellow gum. Chromatography (silica gel, ethyl acetate/cyclohexane 1:1) gives 62 mg (35%) of a slightly yellow solid. MS: m/e=376.3 ($M^+$+H).

EXAMPLE 38

N-[4-(3-Fluoro-benzyloxy)-2-hydroxy-phenyl]-malonamide a) 3-(3-Fluoro-benzyloxy)-phenol Prepared in analogy to example 8 from resorcinol and 3-fluoro-benzylbromide. Colorless oil. Yield=7%. MS: m/e=218.1 ($M^+$).

b) 5-(3-Fluoro-benzyloxy)-2-nitro-phenol 1.0 g (5 mmol) of 3-(3-fluoro-benzyloxy)-phenol is dissolved in 10 ml acetic acid and cooled to 10°. 0.44 g (5 mmol) of 65% nitric acid is dissolved in 10 ml acetic acid and slowly added to the previous solution. The colored mixture is stirred for 15 min. at 10° and for 2 h at room temperature. 50 ml of water is added and the product extracted 3 times with ethyl acetate. Chromatography (silica gel, dichloromethane/methanol 98:2) yields 0.38 g (32%) of the desired product as a yellow solid. MS: m/e=262.1 ($M^+$–H).

c) 2-Amino-5-(3-fluoro-benzyloxy)-phenol

Prepared in analogy to example 8b) by hydrogenation of 5-(3-fluoro-benzyloxy)-2-nitro-phenol. Yield=95%. Greyish solid. MS: m/e=234.3 ($M^+$+H).

d) N-[4-(3-Fluoro-benzyloxy)-2-hydroxy-phenyl]-malonamic acid methyl ester

Prepared in analogy to example 20c) from 2-amino-5-(3-fluoro-benzyloxy)-phenol and methyl malonyl chloride. Yellowish solid. Yield=90%. MS: m/e=334.3 ($M^+$+H).

e) N-[4-(3-Fluoro-benzyloxy)-2-hydroxy-phenyl]-malonamide

Prepared in analogy to example 3 from N-[4-(3-fluoro-benzyloxy)-2-hydroxy-phenyl]-malonamic acid methyl ester and ammonium hydroxide. Yield=23%. Colorless solid. MS: m/e=319.4 ($M^+$+H).

EXAMPLE 39

N-[2-Fluoro-4-(4-fluoro-benzyloxy)-phenyl]-malonamic acid methyl ester a) 1-(2-Fluoro-4-iodo-phenyl)-2,5-dimethyl-1H-pyrrole A solution of 2-fluoro-4-iodoaniline (25.3 g, 107 mmol), acetonylacetone (14.9 g, 131 mmol) and para-toluenesulfonic acid (203 mg, 1 mmol) in dry toluene was heated under reflux for 1 h with a Dean-Stark tap. After cooling to room temperature the mixture was poured into sodium hydrogen carbonate (saturated). The organic layer was separated, washed with brine, dried over sodium sulfate, filtered and then boiled with charcoal. Filtering to remove the charcoal followed by evaporation afforded the title compound (33.2 g, 98%) as a light brown solid. MS: m/e=315.1 ($M^+$+H).

b) 1-[2-Fluoro-4-(4-fluoro-benzyloxy)-phenyl]-2,5-dimethyl-1H-pyrrole

A solution of 1-(2-fluoro-4-iodo-phenyl)-2,5-dimethyl-1H-pyrrole (33.18 g, 105 mmol), 4-fluorobenzylalcohol (26.6 g, 211 mmol), cesium carbonate (68.6 g, 211 mmol), cuprous iodide (2.0 g, 11 mmol) and 1,10-phenanthroline (3.8 g, 21 mmol) in toluene (52 mL) was heated at 100° C. in an autoclave for 48 h. After cooling to room temperature, the mixture was filtered and poured into sodium hydroxide (1N). The resulting mixture was extracted with toluene and the organic extracts washed with brine, dried and evaporated. The residue was triturated with boiling hexane to leave the title compound (24.7 g, 75%) as a light brown solid. MS: m/e=314.1 ($M^+$+H).

c) 2-Fluoro-4-(4-fluoro-benzyloxy)-phenylamine (1:1) hydrochloride

A solution of the 1-[2-fluoro-4-(4-fluoro-benzyloxy)-phenyl]-2,5-dimethyl-1H-pyrrole (23.7 g, 76 mmol), potassium hydroxide (8.5 g, 151 mmol), hydroxylamine HCl (62.5 g, 899 mmol) in water (125 mL) and propan-2-ol (250 mL) was heated at 100° C. for 36 h. After cooling to room temperature, the mixture was poured into water, and extracted with diethylether. The combined organic layers were then washed with brine, dried and the resulting solution was diluted with HCl in diethylether. The resulting precipitate was then filtered off to afford the title compound (15.2 g, 74%) as a light brown solid. MS: m/e=236.0 ($M^+$–Cl).

d) N-[2-Fluoro-4-(4-fluoro-benzyloxy)-phenyl]-malonamic acid methyl ester

The title compound is prepared in analogy to example 1 from 2-fluoro-4-(4-fluoro-benzyloxy)-phenylamine (1:1) hydrochloride. Light yellow solid. Yield=95%. MS: m/e=236.2 ($M^+$+H).

Alternatively the 2-fluoro-4-(4-fluoro-benzyloxy)-phenylamine (1:1) hydrochloride can be prepared as follows.

e) 2-Fluoro-4-(4-fluoro-benzyloxy)-nitrobenzene

A solution of 3-fluoro-4-nitrophenol (5.0 g, 32 mmol) and 4-fluorobenzyl bromide (6.3 g, 33 mmol) in acetone (50 mL) containing potassium carbonate (5.3 g, 38 mmol) was heated under reflux for 2 h. After cooling to room temperature the mixture was filtered and evaporated to leave the title compound (7.3 g, 86%) as a light yellow solid. MS: m/e=265.1 ($M^+$+H).

f) 2-Fluoro-4-(4-fluoro-benzyloxy)-phenylamine (1:1) hydrochloride

A solution of 2-fluoro-4-(4-fluoro-benzyloxy)-nitrobenzene (7.3 g, 27 mmol) in ethyl acetate (160 mL) was hydrogenated in the presence of Pt/C (5%, 1.1 g) at room temperature for 12 h. The mixture was then filtered and HCl in diethylether was added. The resulting precipitate was filtered off and dried to afford the title compound (7.3 g, 99%) as a white solid. MS: m/e=236.2 ($M^+$–Cl).

EXAMPLE 40

N-[2-Fluoro-4-(4-fluoro-benzyloxy)-phenyl]-malonamide

A solution of N-[2-fluoro-4-(4-fluoro-benzyloxy)-phenyl]-malonamic acid methyl ester (150 mg, 0.45 mmol) and ammonium hydroxide (2.0 mL) in THF (1.0 ml) in a sealed tube was heated at 55° C. for 6 h. After cooling to room temperature the mixture was evaporated and the title compound (60 mg, 42%) was purified by trituration from diethylether. MS: m/e=321.2 (M$^+$+H).

EXAMPLE 41

N-[4-(3,5-Bis-trifluoromethyl-benzyloxy)-2-fluoro-phenyl]-malonamic acid methyl ester a) 4-(3,5-Bis-trifluoromethyl-benzyloxy)-2-fluoro-nitrobenzene

As described for example 39e, 3-fluoro-4-nitrophenol (5 g, 32 mmol) was converted to the title compound (12.2 g, 99%) [using 3,5-bis(trifluoromethyl)benzyl bromide (10.3 g, 33 mmol) instead of 4-fluorobenzyl bromide] which was obtained as a light yellow solid. MS: m/e=383.0 (M$^+$).

b) 4-(3,5-Bis-trifluoromethyl-benzyloxy)-2-fluoro-phenylamine (1:1) hydrochloride As described for example 39f, 4-(3,5-bis-trifluoromethyl-benzyloxy)-2-fluoro-nitrobenzene (12.2 g, 32 mmol) was converted to the title compound (8.3 g, 66%) which was obtained as light pink solid. MS: m/e=388.2 (M$^+$−H).

c) N-[4-(3,5-Bis-trifluoromethyl-benzyloxy)-2-fluoro-phenyl]-malonamic acid methyl ester As described for example 39d, 4-(3,5-bis-trifluoromethyl-benzyloxy)-2-fluoro-phenylamine (1:1) hydrochloride (500 mg, 1 mmol) was converted to the title compound (590 mg, 92%) which was obtained as an off-white solid. MS: m/e=454.2 (M$^+$+H).

EXAMPLE 42

N-[4-(3,5-Bis-trifluoromethyl-benzyloxy)-2-fluoro-phenyl]-malonamide

As described for example 40, N-[4-(3,5-bis-trifluoromethyl-benzyloxy)-2-fluoro-phenyl]-malonamic acid methyl ester (250 mg, 0.56 mmol) was converted to the title compound (84 mg, 35%) which was obtained as a white solid after purification by chromatography on silica gel eluting with DCM:MeOH (9:1). MS: m/e=439.2 (M$^+$+H).

EXAMPLE 43

N-[2-Fluoro-4-(4-trifluoromethyl-benzyloxy)-phenyl]-malonamic acid methyl ester a) 2-Fluoro-4-(4-trifluoromethyl-benzyloxy)-nitrobenzene

As described for example 39e, 3-fluoro-4-nitrophenol (5 g, 32 mmol) was converted to the title compound (9.9 g, 99%) [using 3-(trifluoromethyl)benzyl bromide (8.0 g, 33 mmol) instead of 4-fluorobenzyl bromide] which was obtained as a light yellow solid. MS: m/e=315.0 (M$^+$).

b) 2-Fluoro-4-(4-trifluoromethyl-benzyloxy)-phenylamine (1:1) hydrochloride As described for example 39f, 2-fluoro-4-(4-trifluoromethyl-benzyloxy)-nitrobenzene (4.9 g, 15 mmol) was converted to the title compound (3.0 g, 60%) which was obtained as a grey solid.

c) N-[2-Fluoro-4-(4-trifluoromethyl-benzyloxy)-phenyl]-malonamic acid methyl ester As described for example 39d, 2-fluoro-4-(4-trifluoromethyl-benzyloxy)-phenylamine (1:1) hydrochloride (500 mg, 1 mmol) was converted to the title compound (700 mg, 98%) which was obtained as an off-white solid. MS: m/e=386.2 (M$^+$+H).

EXAMPLE 44

N-[2-Fluoro-4-(4-trifluoromethyl-benzyloxy)-phenyl]-malonamide

As described for example 40, N-[2-fluoro-4-(4-trifluoromethyl-benzyloxy)-phenyl]-malonamic acid methyl ester (250 mg, 0.65 mmol) was converted to the title compound (94 mg, 39%) which was obtained as a white solid after purification by chromatography on silica gel eluting with DCM:MeOH (9:1). MS: m/e=371.2 (M$^+$+H).

EXAMPLE 45

N-[4-(3-Fluoro-benzyloxy)-3-methoxy-phenyl]-malonamic acid methyl ester a) 1-(3-Fluoro-benzyloxy)-2)-2-methoxy-4-nitro-benzene

Prepared in analogy to example 8 from 4-nitroguaiacol and 3-fluoro-benzylbromide. Colorless oil. Yield=74%. MS: m/e=277.1 (M$^+$).

b) 4-(3-Fluoro-benzyloxy)-3-methoxy-phenylamine

Prepared in analogy to example 8b) by hydrogenation of 1-(3-fluoro-benzyloxy)-2-methoxy-4-nitro-benzene. The crude reaction mixture was used without purification in the next step.

c) N-[4-(3-Fluoro-benzyloxy)-3-methoxy-phenyl]-malonamic acid methyl ester

Prepared in analogy to example 20c) from 4-(3-fluoro-benzyloxy)-3-methoxy-phenylamine and methyl malonyl chloride. Yellowish solid. Yield=89%. MS: m/e=348.2 (M$^+$+H).

EXAMPLE 46

N-[4-(3-Fluoro-benzyloxy)-3-methoxy-phenyl]-malonamide

Prepared in analogy to example 3 from N-[4-(3-fluoro-benzyloxy)-3-methoxy-phenyl]-malonamic acid methyl ester and 7M ammonia in methanol. Yield=71%. Colorless solid. MS: m/e=333.0 (M$^+$+H).

EXAMPLE 47

N-[4-(3-Fluoro-benzyloxy)-3-methyl-phenyl]-malonamic acid methyl ester a) 1-(3-Fluoro-benzyloxy)-2-methyl-4-nitro-benzene

Prepared in analogy to example 8 from 2-methyl-4-nitrophenol and 3-fluoro-benzylbromide. Colorless oil. Yield=62%. MS: m/e=261.1 (M$^+$).

b) 4-(3-Fluoro-benzyloxy)-3-methyl-phenylamine

Prepared in analogy to example 8b) by hydrogenation of 1-(3-fluoro-benzyloxy)-2-methyl-4-nitro-benzene. The crude reaction mixture was used without purification in the next step.

c) N-[4-(3-Fluoro-benzyloxy)-3-methyl-phenyl]-malonamic acid methyl ester

Prepared in analogy to example 20c) from 4-(3-fluoro-benzyloxy)-3-methyl-phenylamine and methyl malonyl chloride. Colorless solid. Yield=98%. MS: m/e=332.0 ($M^++H$).

EXAMPLE 48

N-[4-(3-Fluoro-benzyloxy)-3-methyl-phenyl]-malonamide

Prepared in analogy to example 3 from N-[4-(3-fluoro-benzyloxy)-3-methyl-phenyl]-malonamic acid methyl ester and 7M ammonia in methanol. Yield=60%. Colorless solid. MS: m/e=317.0 ($M^++H$).

EXAMPLE 49

N-[3-Chloro-4-(3-fluoro-benzyloxy)-phenyl]-malonamic acid methyl ester a) 2-Chloro-1-(3-fluoro-benzyloxy)-4-nitro-benzene Prepared in analogy to example 8 from 2-chloro-4-nitrophenol and 3-fluoro-benzylbromide. Colorless solid. Yield=84%. MS: m/e=281.0 ($M^+$).

b) 3-Chloro-4-(3-fluoro-benzyloxy)-phenylamine

Prepared in analogy to example 8b) by hydrogenation of 2-chloro-1-(3-fluoro-benzyloxy)-4-nitro-benzene. The crude reaction mixture was used without purification in the next step.

c) N-[3-Chloro-4-(3-fluoro-benzyloxy)-phenyl]-malonamic acid methyl ester

Prepared in analogy to example 20c) from 3-chloro-4-(3-fluoro-benzyloxy)-phenylamine and methyl malonyl chloride. Colorless solid. Yield=78%. MS: m/e=352.1 ($M^++H$).

EXAMPLE 50

N-[3-Chloro-4-(3-fluoro-benzyloxy)-phenyl]-malonamide

Prepared in analogy to example 3 from N-[3-chloro-4-(3-fluoro-benzyloxy)-phenyl]-malonamic acid methyl ester and 7M ammonia in methanol. Yield=100%. Colorless solid. MS: m/e=337.1 ($M^++H$).

EXAMPLE 51

Cyclopropane-1,1-dicarboxylic acid amide [2-fluoro-4-(4-fluoro-benzyloxy)-phenyl]-amide A mixture of 2-fluoro-4-(4-fluoro-benzyloxy)-phenylamine (1:1) hydrochloride (272 mg, 1 mmol), 1-carboxycyclopropanecarboxamide (129 mg, 1 mmol), N-(3-dimethylaminopropyl)-N'ethylcarbodiimide hydrochloride (EDCI, 211 mg, 1.1 mmol) and triethylamine (111 mg, 1.1 mmol) in DCM (7 mL) was stirred at rt for 2 h. Then the mixture was poured into water and the mixture extracted with DCM. The combined organic extracts were then dried and evaporated to afford the title compound (130 mg, 38%) as a light brown solid after purification by chromatography on silica gel eluting with ethyl acetate: heptane (1:1 to 3:1). MS: m/e=347.0 ($M^++H$).

EXAMPLE 52

N-[2-Fluoro-4-(4-fluoro-benzyloxy)-phenyl]-2,2-dimethyl-malonamic acid methyl ester A mixture of N-[2-fluoro-4-(4-fluoro-benzyloxy)-phenyl]-malonamic acid methyl ester (335 mg, 1 mmol), sodium hydride (55%, 873 mg, 2 mmol) and iodomethane (213 mg, 1.5 mmol) were stirred at room temperature for 3 h. Then the mixture was poured into water and the mixture extracted with ethyl acetate. The combined organic extracts were then dried and evaporated to afford the title compound (83 mg, 23%) as a light yellow solid after purification by chromatography on silica gel eluting with ethyl acetate: heptane (1:1 to 3:1). MS:m/e=364.1($M^++H$).

EXAMPLE 53

N-[2-Fluoro-4-(4-fluoro-benzyloxy)-phenyl]-malonamic acid ethyl ester

The title compound is prepared in analogy to example 1 from 2-fluoro-4-(4-fluoro-benzyloxy)-phenylamine (1:1) hydrochloride [using ethylmalonyl chloride instead of methylmalonyl chloride]. Light yellow solid. Yield=84%. MS: m/e=350.3 ($M^++H$).

EXAMPLE 54

N-[4-(3-Fluoro-benzyloxy)-3-formyl-phenyl]-malonamic acid methyl ester a) 2-(3-Fluoro-benzyloxy)-5-nitro-benzaldehyde Prepared in analogy to example 8 from 2-hydroxy-5-nitrobenzaldehyde and 3-fluoro-benzylbromide. Colorless solid. Yield=95%. MS: m/e=275.1 ($M^+$).

b) 5-Amino-2-(3-fluoro-benzyloxy)-benzaldehyde

Prepared in analogy to example 8b) by hydrogenation of 2-(3-fluoro-benzyloxy)-5-nitro-benzaldehyde. The crude reaction mixture was used without purification in the next step.

c) N-[4-(3-Fluoro-benzyloxy)-3-formyl-phenyl]-malonamic acid methyl ester

Prepared in analogy to example 20c) from 5-amino-2-(3-fluoro-benzyloxy)-benzaldehyde and methyl malonyl chloride. Colorless solid. Yield=3%. MS: m/e=344.1 ($M^+$–H).

EXAMPLE 55

2-Ethyl-N-[4-(3-fluoro-benzyloxy)-phenyl]-malonamide

A solution of sodium ethanolate is prepared by dissolving 46 mg (2 mmol) sodium in 5 ml ethanol. 302 mg (1 mmol)

of N-[4-(3-fluoro-benzyloxy)-phenyl]-malonamide is added, followed by 343 mg (2 mmol) of ethyl iodide. The reaction mixture is refluxed for 2.5 h, hydrolysed and extracted with ethyl acetate. Chromatography (silica gel; dichloromethane/methanol) yields 45 mg (14%) of a colorless solid. MS: m/e=331.3 (M$^+$+H).

EXAMPLE 56

N-{4-[2-(4-Fluoro-phenyl)-vinyl]-phenyl}-malonamic acid methyl ester a) (4-Nitro-benzyl)-phosphonic acid diethyl ester 10 g (46.3 mmol) of 4-nitrobenzylbromide and 10.03 g (60.3 mmol) of triethyl phosphite are dissolved in 25 ml dimethylformamide. The reaction mixture is held at 155° C. for 1.5 h, diluted with 20 ml water and extracted 3 times with ethyl acetate. The organic phase is dried and concentrated to yield 8.35 g (66%) of the crude title compound. MS: m/e=274.1 (M$^+$+H).

b) 4-[2-(4-Fluoro-phenyl)-vinyl]-1-nitro-benzene 2.63 g of sodium hydride are added to 50 ml of dimethylformamide. The mixture is cooled to 0° C. and 16 g (58.6 mmol) of (4-nitro-benzyl)-phosphonic acid diethyl ester is added portionwise. The solution is stirred at room temperature for 1.5 h, then cooled to −10°. A solution of 6.09 g (50 mmol)4-fluoro-benzaldehyde in 10 ml dimethylformamide is slowly added to the mixture at −10°. Stirring at room temperature for 45 min followed by additon of 250 ml water yields a precipitate which is filtered and recrystallised from ethanol/water 85:15 to yield 10.81 g (91%) of a yellow solid. MS: m/e=243.1 (M$^+$).

c) 4-[2-(4-Fluoro-phenyl)-vinyl]-phenylamine

A solution of 7.3 g (30 mmol) of 4-[2-(4-fluoro-phenyl)-vinyl]-1-nitro-benzene in 250 ml of ethanol is treated with 80 ml of aqueous 25% hydrochloric acid. The mixture is heated at 110° C. and 5 g (42 mmol) of tin is added portionwise. After stirring for 3 h at 110° C. the suspension is cooled to room temperature, neutralised by additon of aqueous sodium hydroxide and extracted 3 times with dichloromethane. Drying over magnesium sulfate and evaporations yields 5.46 g (85%) of a colorless solid. MS: m/e=214.2 (M$^+$+H).

d) N-{4-[2-(4-Fluoro-phenyl)-vinyl]-phenyl}-malonamic acid methyl ester

Prepared in analogy to example 20c) from 4-[2-(4-fluoro-phenyl)-vinyl]-phenylamine and methyl malonyl chloride. Colorless solid. Yield=97%. MS: m/e=314.0 (M$^+$+H).

EXAMPLE 57

N-{4-[2-(4-Fluoro-phenyl)-vinyl]-phenyl}-malonamide

Prepared in analogy to example 3 from N-{4-[2-(4-fluoro-phenyl)-vinyl]-phenyl}-malonamic acid methyl ester and 7M ammonia in methanol. Yield=89%. Colorless solid. MS: m/e=299.2 (M$^+$+H).

EXAMPLE 58

N-{4-[2-(3-Fluoro-phenyl)-vinyl]-phenyl}-malonamic acid methyl ester a) 4-[2-(3-Fluoro-phenyl)-vinyl]-1-nitro-benzene Prepared in analogy to example 56b) from (4-nitro-benzyl)-phosphonic acid diethyl ester and 3-fluoro-benzaldehyde. Yellow solid. Yield=82%. MS: m/e=243.0 (M$^+$).

b) 4-[2-(3-Fluoro-phenyl)-vinyl]-phenylamine 2.41 g (10 mmol) of 4-[2-(3-fluoro-phenyl)-vinyl]-1-nitro-benzene is dissolved in 25 ml of ethyl acetate and treated with 240 mg of platinum 5% on charcoal. Hydrogenation is performed at room temperature and normal pressure for 4 h. The catalyst is filtered off and the filtrate concentrated. The residue is crystallised from diethyl ether/heptane to yield 1.32 g (62%) of an orange solid. MS: m/e=213.1 (M$^+$).

c) N-{4-[2-(3-Fluoro-phenyl)-vinyl]-phenyl}-malonamic acid methyl ester

Prepared in analogy to example 20c) from 4-[2-(3-fluoro-phenyl)-vinyl]-phenylamine and methyl malonyl chloride. Colorless solid. Yield=99%. MS: m/e=313.9 (M$^+$+H).

EXAMPLE 59

N-{4-[2-(3-Fluoro-phenyl)-vinyl]-phenyl}-malonamide

Prepared in analogy to example 3 from N-{4-[2-(3-fluoro-phenyl)-vinyl]-phenyl}-malonamic acid methyl ester and 7M ammonia in methanol. Yield=68%. Colorless solid. MS: m/e=299.2 (M$^+$+H).

EXAMPLE 60

N-{4-[2-(4-Fluoro-phenyl)-ethyl]-phenyl}-malonamic acid methyl ester a) 4-[2-(4-Fluoro-phenyl)-ethyl]-phenylamine 3.46 g of 4-[2-(4-fluoro-phenyl)-vinyl]-phenylamine is dissolved in 100 ml of tetrahydrofuran, treated with 350 mg of palladium 10% on charcoal and hydrogenated at room temperature and normal pressure for about 4 h. The catalyst is filtered off and the filtrate concentrated to yield 3.46 g (99%) of a yellow solid. MS: m/e=216.9 (M$^+$+H).

b) N-{4-[2-(4-Fluoro-phenyl)-ethyl]-phenyl}-malonamic acid methyl ester

Prepared in analogy to example 20c) from 4-[2-(4-fluoro-phenyl)-ethyl]-phenylamine and methyl malonyl chloride. Colorless solid. Yield=99%. MS: m/e=316.0 (M$^+$+H).

EXAMPLE 61

N-{4-[2-(4-Fluoro-phenyl)-ethyl]-phenyl}-malonamide

Prepared in analogy to example 3 from N-{4-[2-(4-fluoro-phenyl)-ethyl]-phenyl}-malonamic acid methyl ester and 7M ammonia in methanol. Yield=94%. Colorless solid. MS: m/e=301.1 (M$^+$+H).

EXAMPLE 62

N-{4-[2-(3-Fluoro-phenyl)-ethyl]-phenyl}-malonamic acid methyl ester a) [2-(3-Fluoro-phenyl)-ethyl]-phenylamine Prepared in analogy to example 60a) by hydrogenation of 4-[2-(3-fluoro-phenyl)-vinyl]-phenylamine. Yellow solid. Yield=100%. MS: m/e=215.1 (M$^+$).

b) N-{4-[2-(3-Fluoro-phenyl)-ethyl]-phenyl}-malonamic acid methyl ester

Prepared in analogy to example 20c) from 4-[2-(3-fluoro-phenyl)-ethyl]-phenylamine and methyl malonyl chloride. Colorless solid. Yield=95%. MS: m/e=316.0 (M$^+$+H).

EXAMPLE 63

N-{4-[2-(4-Methoxy-phenyl)-vinyl]-phenyl}-malonamic acid methyl ester a) 4-[2-(4-Methoxy-phenyl)-vinyl]-phenylamine Prepared in analogy to example 56b) from (4-nitro-benzyl)-phosphonic acid diethyl ester and 4-methoxy-benzaldehyde. Yellow solid. Yield=69%. MS: m/e=225.9 (M$^+$).

b) m N-{4-[2-(4-Methoxy-phenyl)-vinyl]-phenyl}-malonamic acid methyl ester

Prepared in analogy to example 20c) from 4-[2-(4-methoxy-phenyl)-vinyl]-phenylamine and methyl malonyl chloride. Colorless solid. Yield=66%. MS: m/e=326.1 (M$^+$+H).

EXAMPLE 64

N-{4-[2-(4-Chloro-phenyl)-ethyl]-phenyl}-malonamic acid methyl ester a) 4-[2-(4-Chloro-phenyl)-vinyl]-1-nitro-benzene Prepared in analogy to example 56b) from (4-nitro-benzyl)-phosphonic acid diethyl ester and 4-chloro-benzaldehyde. Yellow solid. Yield=95%. MS: m/e=259.1 (M$^+$).

b) 4-[2-(4-Chloro-phenyl)-ethyl]-phenylamine

A solution of 5.0 g (19.2 mmol) 4-[2-(4-chloro-phenyl)-vinyl]-1-nitro-benzene in 100 ml ethyl acetate is treated with 200 mg of platinum 5% on charcoal. Hydrogenation is performed at room temperature and normal pressure overnight. The catalyst is filtered off and the filtrate evaporated to yield 3.17 g (71%) of a slightly yellow solid. MS: m/e=231.9 (M$^+$+H).

c) N-{4-[2-(4-Chloro-phenyl)-ethyl]-phenyl}-malonamic acid methyl ester

Prepared in analogy to example 20c) from 4-[2-(4-chloro-phenyl)-ethyl]-phenylamine and methyl malonyl chloride. Colorless solid. Yield=99%. MS: m/e=332.1 (M$^+$+H).

EXAMPLE 65

N-{4-[2-(4-Chloro-phenyl)-ethyl]-phenyl}-malonamide

Prepared in analogy to example 3 from N-{4-[2-(4-chloro-phenyl)-ethyl]-phenyl}-malonamic acid methyl ester and 7M ammonia in methanol. Yield=65%. Colorless solid. MS: m/e=317.1 (M$^+$+H).

EXAMPLE 66

2-Amino-N-[2-fluoro-4-(4-fluoro-benzyloxy)-phenyl]-acetamide (1:1) hydrochloride a) {[2-Fluoro-4-(4-fluoro-benzyloxy)-phenylcarbamoyl]-methyl}-carbamic acid tert-butyl ester A mixture of 2-fluoro-4-(4-fluoro-benzyloxy)-phenylamine (1:1) hydrochloride (272 mg, 1 mmol), Boc-glycine (263 mg, 1.5 mmol), N,N'-dicylcohexylcarbodiimide (206 mg, 1 mmol) and pyridine (127 mg, 1.6 mmol) in ethyl acetate (6 mL) was stirred at room temperature for 3 h. After this time, the reaction mixture wa poured into sodium hydrogen carbonate (saturated), and the mixture extracted with ethyl acetate. The combined organic layers were then washed with brine and dried. Filtration and evaporation afforded the title compound (180 mg, 46%) as a light brown solid after chromatography on silica gel eluting with ethyl acetate:heptane (1:1 to 4:1). MS: m/e=393.1 (M$^+$+H).

b) 2-Amino-N-[2-fluoro-4-(4-fluoro-benzyloxy)-phenyl]-acetamide (1:1) hydrochloride A solution of {[2-fluoro-4-(4-fluoro-benzyloxy)-phenylcarbamoyl]-methyl}-carbamic acid tert-butyl ester (148 mg, 0.4 mmol) in HCl dioxane (4 M, 3 mL) was stirred at room temperature for 1 h. The resulting precipitate was filtered off to afford the title compound (112 mg, 90%) as a white solid. MS: m/e=293.1 (M$^+$−Cl).

EXAMPLE 67

(R)-2-Amino-N-[2-fluoro-4-(4-fluoro-benzyloxy)-phenyl]-propionamide

As described for example 66a and 66b, 2-fluoro-4-(4-fluoro-benzyloxy)-phenylamine (1:1) hydrochloride (200 mg, 0.7 mmol) was converted to the title compound (127 mg, 39%) [using Boc-D-Ala-OH instead of Boc-glycine] which was obtained as a white solid. MS: m/e=307.0 (M$^+$−Cl).

EXAMPLE 68

2-Amino-N-[2-fluoro-4-(4-fluoro-benzyloxy)-phenyl]-propionamide

As described for example 66a and 66b, 2-fluoro-4-(4-fluoro-benzyloxy)-phenylamine (1:1) hydrochloride (200 mg, 0.7 mmol) was converted to the title compound (41 mg, 15%) [using Boc-DL-Ala-OH instead of Boc-glycine] which was obtained as a white solid. MS: m/e=306.9 (M$^+$+H).

EXAMPLE 69

1-[2-Fluoro-4-(4-fluoro-benzyloxy)-phenylcarbamoyl]-2S-methyl-propyl-ammonium; chloride As described for example 66a and 66b, 2-fluoro-4-(4-fluoro-benzyloxy)-phenylamine (1:1) hydrochloride (200 mg, 0.7 mmol) was converted to the title compound (47 mg, 12%) [using Boc-L-Valine instead of Boc-glycine] which was obtained as a white solid. MS: m/e=335.2 (M$^+$+H).

EXAMPLE 70

2-Acetylamino-N-[2-fluoro-4-(4-fluoro-benzyloxy)-phenyl]-acetamide

A solution of 2-amino-N-[2-fluoro-4-(4-fluoro-benzyloxy)-phenyl]-acetamide (1:1) hydrochloride (50 mg, 0.15 mmol), acetyl chloride (14.4 mg, 0.18 mmol), triethylamine (31 mg, 0.30 mmol) was stirred at 0° C. for 4 h. Then

EXAMPLE 71

(R)-2-Acetylamino-N-[2-fluoro-4-(4-fluoro-benzyloxy)-phenyl]-propionamide

As described for example 70, (R)-2-amino-N-[2-fluoro-4-(4-fluoro-benzyloxy)-phenyl]-propionamide (50 mg, 0.15 mmol) was converted to the title compound (43 mg, 76%) which was obtained as a white solid. MS: m/e=349.4 ($M^++H$).

EXAMPLE 72

N-[2-Fluoro-4-(4-fluoro-benzyloxy)-phenyl]-2-formylamino-acetamide

Step 1: A mixture of acetic anhydride (40 mg, 0.39 mmol) and formic acid (22 mg, 0.48 mmol) was stirred at 0° C. and then heated uat 60° C. for 1 h. Step 2: During this time, 2-amino-N-[2-fluoro-4-(4-fluoro-benzyloxy)-phenyl]-acetamide (1:1) hydrochloride (50 mg, 0.15 mmol) was extracted with DCM and sodium hydrogen carboante (saturated) and the organic layer evaporated. Then to a mixture of the acetic formic anhydride (Step 1) in dry THF (0.5 mL) was added a solution of the amine (Step 2) in dry THF (1 mL) at room temperature and the resulting mixture stirred for 10 min. Then the reaction mixture was evaporated leave the title compound (44.1 mg, 91%) as a white solid. MS: m/e=321.1 ($M^++H$).

EXAMPLE 73

(R)-N-[2-Fluoro-4-(4-fluoro-benzyloxy)-phenyl]-2-formylamino-propionamide

As described for example 72, (R)-2-amino-N-[2-fluoro-4-(4-fluoro-benzyloxy)-phenyl]-propionamide (50 mg, 0.15 mmol) was converted to the title compound (16 mg, 30%) which was obtained as a white solid. MS: m/e=333.1 ($M^+-H$).

EXAMPLE 74

2-Amino-N-[2-fluoro-4-(3-fluoro-benzyloxy)-phenyl]-acetamide hydrochloride (1:1)

As described for example 66a and 66b, 2-fluoro-4-(3-fluoro-benzyloxy)-phenylamine (1:1) hydrochloride (500 mg, 2.1 mmol) was converted to the title compound (300 mg, 44%) which was obtained as a white solid. MS: m/e= 293.1 ($M^+-Cl$).

EXAMPLE 75

2-Acetylamino-N-[2-fluoro-4-(3-fluoro-benzyloxy)-phenyl]-acetamide

As described for example 70, 2-fluoro-4-(3-fluoro-benzyloxy)-phenylamine (1:1) hydrochloride (150 mg, 0.45 mmol) was converted to the title compound (127 mg, 84%) which was obtained as a white solid. MS: m/e=335.2 ($M^++H$).

EXAMPLE 76

N-[2-Fluoro-4-(3-fluoro-benzyloxy)-phenyl]-2-formylamino-acetamide

As described for example 72, 2-fluoro-4-(3-fluoro-benzyloxy)-phenylamine (1:1) hydrochloride (133 mg, 0.4 mmol) was converted to the title compound (115 mg, 89%) which was obtained as a white solid. MS: m/e=321.1 ($M^++H$).

EXAMPLE 77

2-Amino-N-[2-fluoro-4-(4-trifluoromethyl-benzyloxy)-phenyl]-acetamide (1:1) hydrochloride As described for example 66a and 66b, 2-fluoro-4-(4-trifluoromethyl-benzyloxy)-phenylamine (1:1) hydrochloride (600 mg, 2.1 mmol) was converted to the title compound (155 mg, 20%) which was obtained as a white solid. MS: m/e=343.1 ($M^+-Cl$).

EXAMPLE 78

2-Acetylamino-N-[2-fluoro-4-(4-trifluoromethyl-benzyloxy)-phenyl]-acetamide

As described for example 70, 2-fluoro-4-(4-trifluoromethyl-benzyloxy)-phenylamine (1:1) hydrochloride (120 mg, 0.32 mmol) was converted to the title compound (119 mg, 98%) which was obtained as a white solid. MS: m/e=385.2 ($M^++H$).

EXAMPLE 79

2-Amino-N-[4-(3,5-bis-trifluoromethyl-benzyloxy)-2-fluoro-phenyl]-acetamide (1:1) hydrochloride As described for example 66a and 66b, 4-(3,5-bis-trifluoromethyl-benzyloxy)-2-fluoro-phenylamine (1:1) hydrochloride (500 mg, 1.4 mmol) was converted to the title compound (180 mg, 30%) which was obtained as a white solid. MS: m/e=411.2 ($M^+-Cl$).

EXAMPLE 80

2-Acetylamino-N-[4-(3,5-bis-trifluoromethyl-benzyloxy)-2-fluoro-phenyl]-acetamide As described for example 70, 4-(3,5-bis-trifluoromethyl-benzyloxy)-2-fluoro-phenylamine (1:1) hydrochloride (130 mg, 0.29 mmol) was converted to the title compound (107 mg, 81%) which was obtained as a white solid. MS: m/e= 453.2 ($M^++H$).

EXAMPLE 81

2-Amino-N-[4-(3-fluoro-benzyloxy)-phenyl]-acetamide; hydrochloride a) {[4-(3-Fluoro-benzyloxy)-phenylcarbamoyl]-methyl}-carbamic acid tert-butyl ester A mixture of 0.345 g (1.59 mmol) 4-(3-fluoro-benzyloxy)-phenylamine and 0.278 g (1.59 mmol) of N-tert-Butyloxyglycine is dissolved in 10 ml of ethyl acetate, cooled to 0° and 0.328 g (1.59 mmol) N,N'-dicyclohexylcarbodiimide is added at once. The resulting slurry is stirred for additional 3 h at room temperature and filtered. The filtrate is washed 3 times with saturated sodium carbonate solution, dried and concentrated. The residue is triturated with 20 ml diethylether to give 0.353 g (59%) of the title compound as a colorless solid. MS: m/e=375.4 ($M^+$+H).

b) 2-Amino-N-[4-(3-fluoro-benzyloxy)-phenyl]-acetamide; hydrochloride

A slurry of 0.166 g (0.44 mmol) of {[4-(3-fluoro-benzyloxy)-phenylcarbamoyl]-methyl}-carbamic acid tert-butyl ester in 1 ml diethyl ether is treated with 3 ml of a saturated solution of gaseous hydrochloric acid in diethyl ether. The mixture is refluxed for 4 h, poured on water and made basic by addition of a saturated sodium carbonate solution. Extraction with ethyl acetate yields a yellowish solid which is dissolved in about 1 ml of diethyl ether and treated with a few drops of a saturated solution of gaseous hydrochloric acid in diethyl ether. The precipitate is filtered to give 0.051 g (37%) of a colorless solid. MS: m/e=275.2 ($M^+$+H).

The following Examples A to C are prophetic.

EXAMPLE A

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

An injection solution may have the following composition and is manufactured in usual manner:

|  | |
| --- | --- |
| Active substance | 1.0 mg |
| 1N HCl | 20.0 µl |
| acetic acid | 0.5 mg |
| NaCl | 8.0 mg |
| phenol | 10.0 mg |
| 1N NaOH | q.s. ad pH 5 |
| $H_2O$ | q.s. ad 1 ml |

What is a claimed:
1. A compound of the formula:

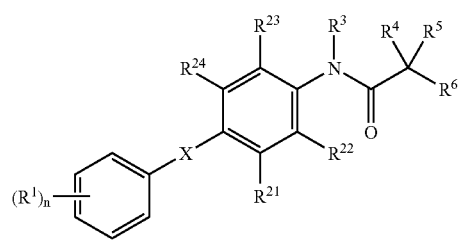

wherein $R_1$ is halogen, halogen-$(C_1-C_6)$-alkyl, cyano, $(C_1-C_6)$-alkoxy or halogen-$(C_1-C_6)$-alkoxy;

$R^{21}$, $R^{22}$, $R^{23}$ and $R^{24}$ are each independently selected from the group consisting of hydrogen, $(C_1-C_6)$-alkyl, halogen, halogen-$(C_1-C_6)$-alkyl, hydroxy, $(C_1-C_6)$-alkoxy or —CHO;

$R^3$ is hydrogen or $(C_1-C_3)$-alkyl;

$R^4$, $R^5$ are each independently selected from the group consisting of hydrogen, $(C_1-C_6)$-alkyl, $(C_1-C_6)$-alkoxy or —COO$(C_1-C_6)$alkyl, or, alternatively, $R^4$ and $R^5$, together with the C-atom to which they are attached, for a $(C_3-C_7)$-cycloalkyl ring;

$R^6$ is —CO—NR$^7$R$^8$, —COO$(C_1-C_6)$-alkyl, or —NHC(O)R;

$R^7$ and $R^8$ are each independently selected from the group consisting of hydrogen, $(C_1-C_6)$-alkyl, $NH_2$ or hydroxy;

R is hydrogen or $(C_1-C_6)$-alkyl;

n is 0, 1, 2 or 3;

X is —CHRO, —OCHR—, —CH₂S—, —SCH₂—, —CH₂CH₂—, —CH═CH— or —C≡C—; or a pharmaceutically acceptable salt thereof.

2. A compound of claim 1, wherein X is CH₂O.

3. A compound of claim 2, wherein R¹ is halogen or halogen(C₁–C₆)alkyl.

4. A compound of claim 3, wherein R⁶ is CONH₂.

5. The compound of claim 4, which is N-[4-(3-fluoro-benzyloxy)-phenyl]-malonamide.

6. A compound of claim 3, wherein R⁶ is COOCH₃.

7. The compound of claim 6, which is N-[4-(3-fluoro-benzyloxy)-phenyl]-malonamic acid methyl ester.

8. A pharmaceutical composition comprising a therapeutically effective amount of a compound of the formula:

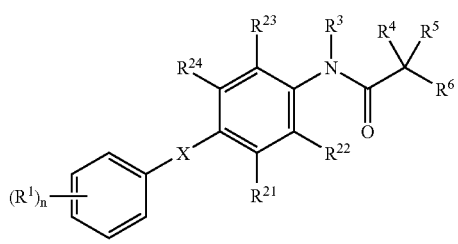

I wherein
R¹ is halogen, halogen-(C₁–C₆)-alkyl, cyano, (C₁–C₆)-alkoxy or halogen-(C₁–C₆)-alkoxy;

R²¹, R²², R²³ and R²⁴ are each independently selected from the group consisting of hydrogen, (C₁–C₆)-alkyl, halogen, halogen-(C₁–C₆)-alkyl, hydroxy, (C₁–C₆)-alkoxy or —CHO;

R³ is hydrogen or (C₁–C₃)-alkyl;

R⁴, R⁵ are each independently selected from the group consisting of hydrogen, (C₁–C₆)-alkyl, (C₁–C₆)-alkoxy or —COO(C₁–C₆)alkyl, or, alternatively, R⁴ and R⁵, together with the C-atom to which they are attached, for a (C₃–C₇)-cycloalkyl ring;

R⁶ is —CO—NR⁷R⁸, —COO(C₁–C₆)-alkyl, —CN, or —NHC(O)R;

R⁷ and R⁸ are each independently selected from the group consisting of hydrogen, (C₁–C₆)-alkyl, NH₂ or hydroxy;

R is hydrogen or (C₁–C₆)-alkyl;

n is 0, 1, 2 or 3;

X is —CHRO, —OCHR—, —CH₂S—, —SCH₂—, —CH₂CH₂—, —CH═CH— or —C≡C—; or a pharmaceutically acceptable salt thereof.

9. A composition of claim 8, wherein the compound is N-[4-(3-fluoro-benzyloxy)-phenyl]-malonamide.

10. A composition of claim 8, wherein the compound is N-[4-(3-fluoro-benzyloxy)-phenyl]-malonamic acid methyl ester.

* * * * *